United States Patent
McNaughton-Smith et al.

(10) Patent No.: US 6,593,349 B2
(45) Date of Patent: Jul. 15, 2003

(54) BISARYLAMINES AS POTASSIUM CHANNEL OPENERS

(75) Inventors: Grant Andrew McNaughton-Smith, Morrisville, NC (US); George Salvatore Amato, Cary, NC (US)

(73) Assignee: ICAgen, Inc., Durham, NC (US)

( * ) Notice: Subject to any disclaimer, the term of this patent is extended or adjusted under 35 U.S.C. 154(b) by 0 days.

(21) Appl. No.: 10/095,617

(22) Filed: Mar. 11, 2002

(65) Prior Publication Data

US 2002/0193597 A1 Dec. 19, 2002

Related U.S. Application Data

(60) Provisional application No. 60/277,329, filed on Mar. 19, 2001.

(51) Int. Cl.$^7$ .................. C07D 401/02; A61K 31/44
(52) U.S. Cl. .................. 514/333; 514/256; 514/338; 514/373; 514/379; 514/405; 544/333; 546/256; 546/271.1; 546/272.1; 546/275.7; 548/213; 548/246; 548/362.1
(58) Field of Search ..................... 546/115, 119, 546/194, 256, 271.1, 272.1, 275.7; 548/213, 246, 362.1; 544/333; 514/256, 333, 338, 373, 379, 408

(56) References Cited

FOREIGN PATENT DOCUMENTS

WO    WO 98/14450 A1    4/1988

*Primary Examiner*—Zinna Northington Davis
(74) *Attorney, Agent, or Firm*—Townsend and Townsend and Crew LLP

(57) ABSTRACT

Compounds, compositions and methods are provided which are useful in the treatment of diseases through the modulation of potassium ion flux through voltage-dependent potassium channels. More particularly, the invention provides bisarylamines, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases) and as neuroprotective agents (e.g., to prevent stroke and the like) by opening potassium channels associated with the onset or recurrence of the indicated conditions.

67 Claims, 11 Drawing Sheets

54

55

56

57

58

59

60

61

62

63

64

65

66

BISARYLAMINES AS POTASSIUM CHANNEL OPENERS

CROSS-REFERENCES TO RELATED APPLICATIONS

The present application claims priority to U.S. Provisional Patent Application Ser. No. 60/277,329, filed on Mar. 19, 2001, the disclosure of which is incorporated herein by reference in its entirety for all purposes.

FIELD OF THE INVENTION

This invention relates to the use of certain bisarylamines as potassium channel openers and to the treatment of diseases modulated by potassium channel opening. Additionally, this invention relates to novel compounds that are useful as potassium channel openers.

BACKGROUND OF THE INVENTION

Ion channels are cellular proteins that regulate the flow of ions, including calcium, potassium, sodium and chloride, into and out of cells. These channels are present in all human cells and affect such processes as nerve transmission, muscle contraction and cellular secretion. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels have now been associated with a number of physiological processes, including regulation of heartbeat, dilation of arteries, release of insulin, excitability of nerve cells, and regulation of renal electrolyte transport. Potassium channels are made by alpha subunits that fall into at least 8 families, based on predicted structural and functional similarities (Wei et al., *Neuropharmacology* 35(7): 805–829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066–71 (1997)) and are gated by both voltage and calcium or pH (Schreiber et al., *J. Biol. Chem.* 273: 3509–16 (1998)). Another family, the inward rectifier potassium channels (Kir), belongs to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625–633 (1996); Shi et al., *Neuron* 16(4): 843–852 (1996)). In another example, the KQT family beta subunit, minK, primarily changes activation kinetics (Sanguinetti et al., *Nature* 384: 80–83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261: 221–224 (1993); Schreiber et al., *J. Biol. Chem.*, 273: 3509–16 (1998); and Joiner et al., *Nature Neurosci.* 1: 462–469 (1998)). These Slo family members have been shown to be voltage and/or calcium gated, and/or regulated by intracellular pH.

Certain members of the Kv family of potassium channels were recently renamed (see, Biervert, et al., *Science* 279: 403–406 (1998)). KvLQT1 was re-named KCNQ1, and the KvLQT1-related channels (KvLR1 and KvLR2) were renamed KCNQ2 and KCNQ3, respectively. More recently, additional members of the KCNQ subfamily were identified. For example, KCNQ4 was identified as a channel expressed in sensory outer hair cells (Kubisch, et al., *Cell* 96(3): 437–446 (1999)). KCNQ5 (Kananura et al., *Neuroreport* 11(9):2063 (2000)), KCNQ 2/3 (Main et al., *Mol. Pharmacol.* 58: 253–62 (2000), KCNQ 3/5 (Wickenden et al., *Br. J. Pharma* 132: 381(2001)) and KCNQ6 have also recently been described.

KCNQ2 and KCNQ3 have been shown to be nervous system-specific potassium channels associated with benign familial neonatal convulsions ("BFNC"), a class of idiopathic generalized epilepsy (see, Leppert, et al., *Nature* 337: 647–648 (1989)). These channels have been linked to M-current channels (see, Wang, et al., *Science* 282: 1890–1893 (1998)). The discovery and characterization of these channels and currents provides useful insights into how these voltage dependent (Kv) potassium channels function in different environments, and how they respond to various activation mechanisms. Such information has now led to the identification of modulators of KCNQ2 and KCNQ3 potassium channels or the M-current, and the use of such modulators as therapeutic agents. The modulators are the subject of the present invention.

SUMMARY OF THE INVENTION

The present invention provides bisarylamines and pharmaceutically acceptable salts thereof ("compounds of the invention"), which are useful in the treatment of diseases through the modulation of potassium ion flux through voltage-dependent potassium channels.

In one aspect, the present invention provides compounds of the formula:

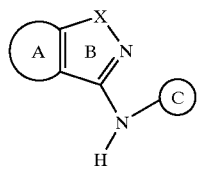
(I)

in which the ring designated by the letter A is fused at two points to the ring designated by the letter B. Ring A is a substituted or unsubstituted aryl ring or it is a five- or six-membered, substituted or unsubstituted heteroaryl ring.

The ring designated by the letter C is a heteroaromatic ring selected from the formulae:

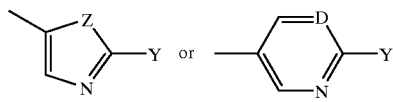

in which the letter Z represents $NR^o$, S or O. The letter D represents N or $CR^1$, and the letter Y represents halogen, $R^2$, or $OR^2$. The symbols $R^o$, $R^1$ and $R^2$ each independently represent hydrogen, substituted alkyl, or unsubstituted alkyl.

The letter X represents —N($R^3$)—, —O—, —C(O)—, or —S(O)$_n$—, in which the letter n represents an integer from 0 to 2. The symbol $R^3$ represents a group selected from hydrogen, SO$_2$R$^4$, substituted or unsubstituted alkyl and cycloalkyl. $R^4$ is a substituted or unsubstituted alkyl group or a cycloalkyl group. Preferred cycloalkyl groups are $C_3$ to $C_5$ cycloalkyl groups, and preferred substituted or unsubstituted alkyl groups are $C_1$ to $C_3$ groups.

In another aspect, the present invention provides pharmaceutical compositions comprising a pharmaceutically acceptable excipient and a compound of the formula provided above.

In yet another aspect, the present invention provides a method for increasing flow through voltage dependent potassium channels in a cell, comprising contacting the cell with a compound of the formula provided above in an amount sufficient to open the potassium channels.

In still another aspect, the present invention provides a method for treating a central or peripheral nervous system disorder or condition through the modulation of a voltage-dependent potassium channel, the method comprising administering to a subject in need of such treatment an effective amount of a compound of the formula provided above.

Other objects and advantages of the present invention will be apparent from the detailed description that follows.

DETAILED DESCRIPTION OF THE INVENTION AND THE PREFERRED EMBODIMENTS

Abbreviations and Definitions

Figure 1:
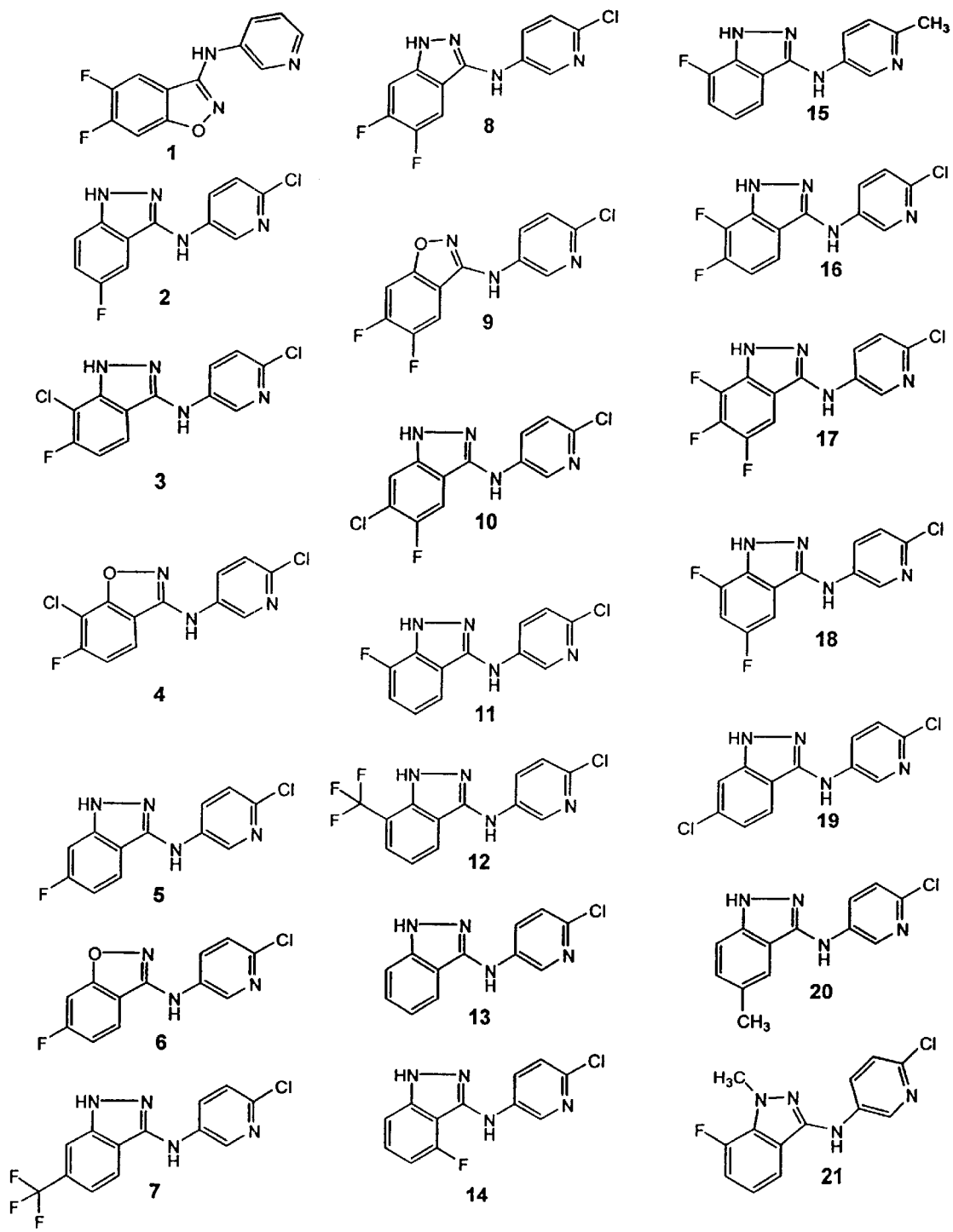
FIG. 1 displays structures of representative compounds of the invention.
Figure 1:
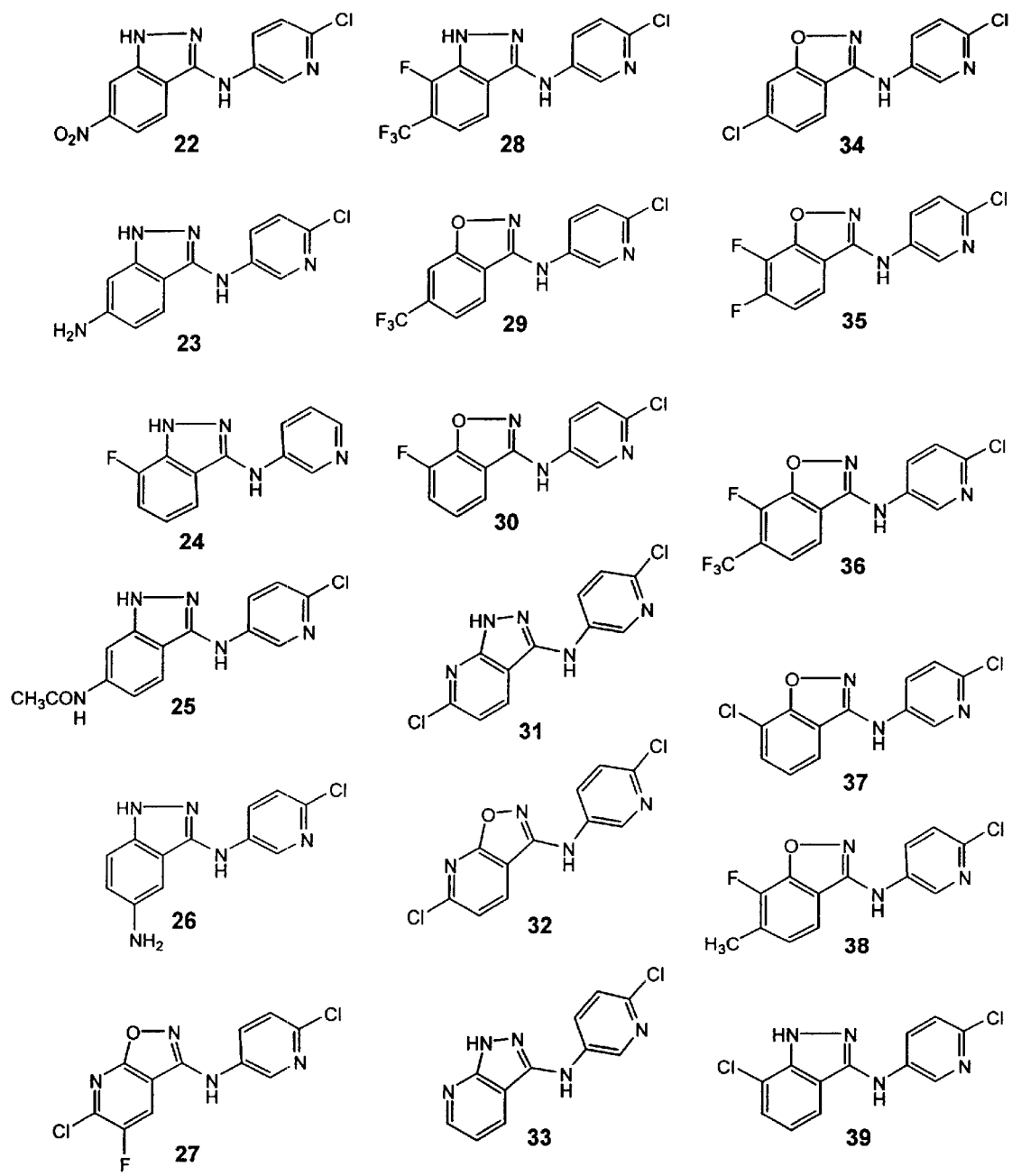
Figure 1:
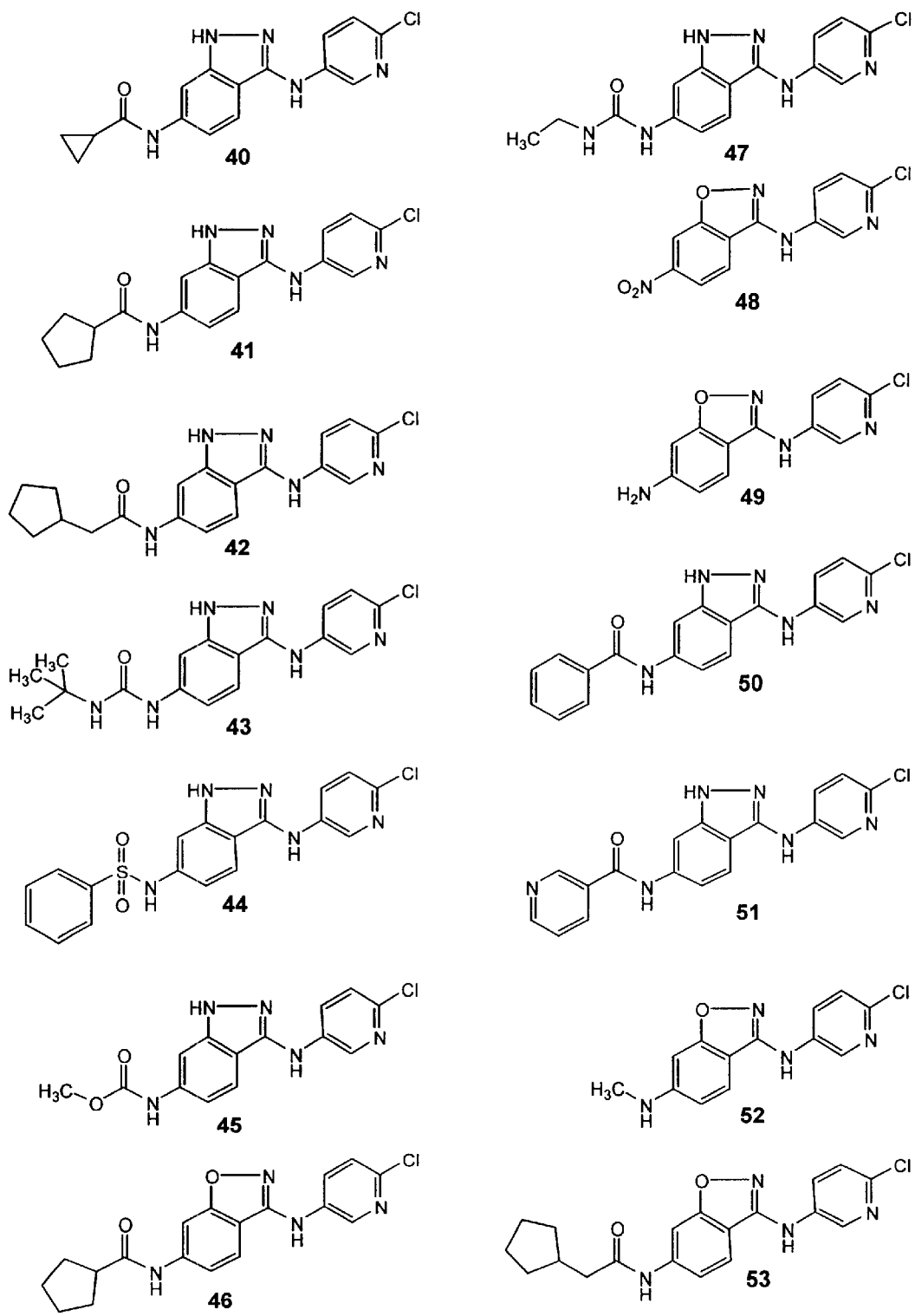
Figure 1:
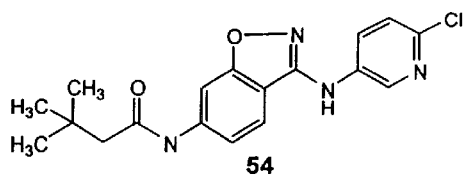
Figure 1:
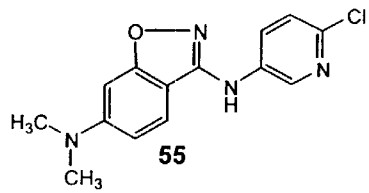
Figure 1:
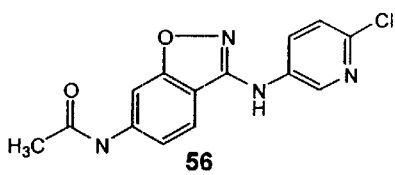
Figure 1:
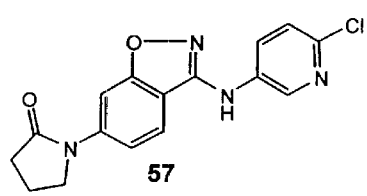
Figure 1:
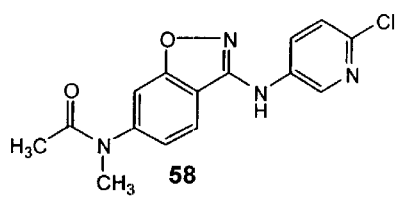
Figure 1:
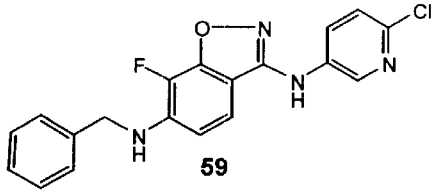
Figure 1:
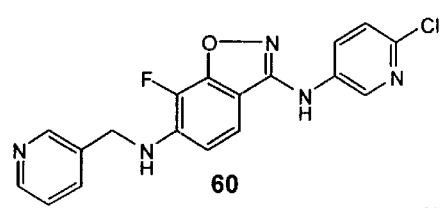
Figure 1:
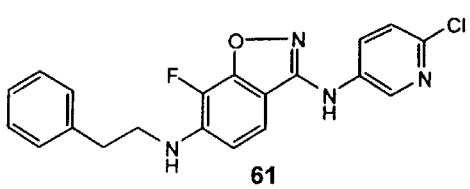
Figure 1:
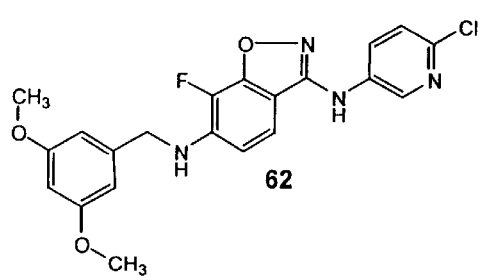
Figure 1:
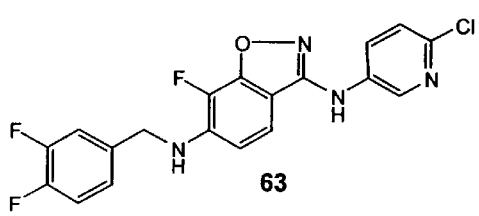
Figure 1:
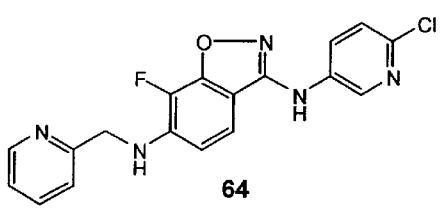
Figure 1:
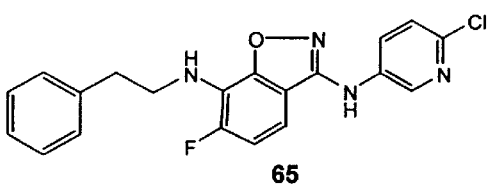
Figure 1:
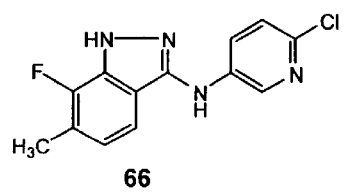
Figure 1:
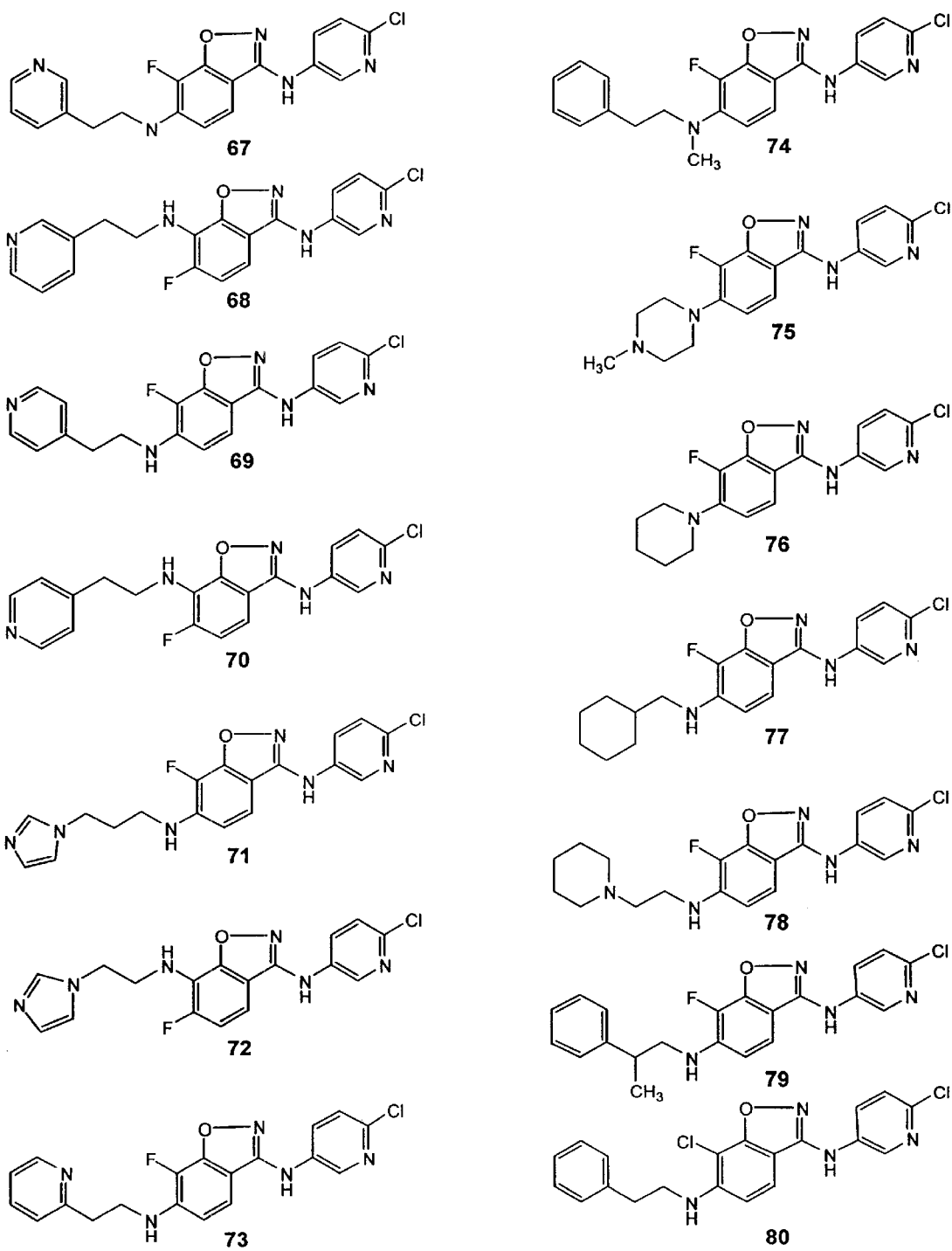
Figure 1:
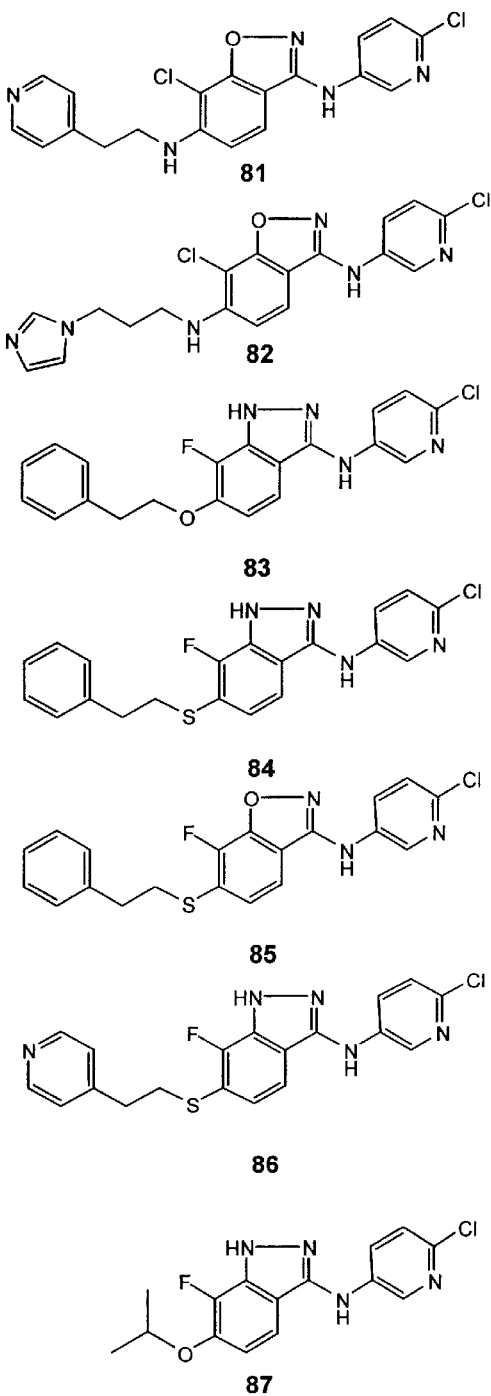
Figure 1:
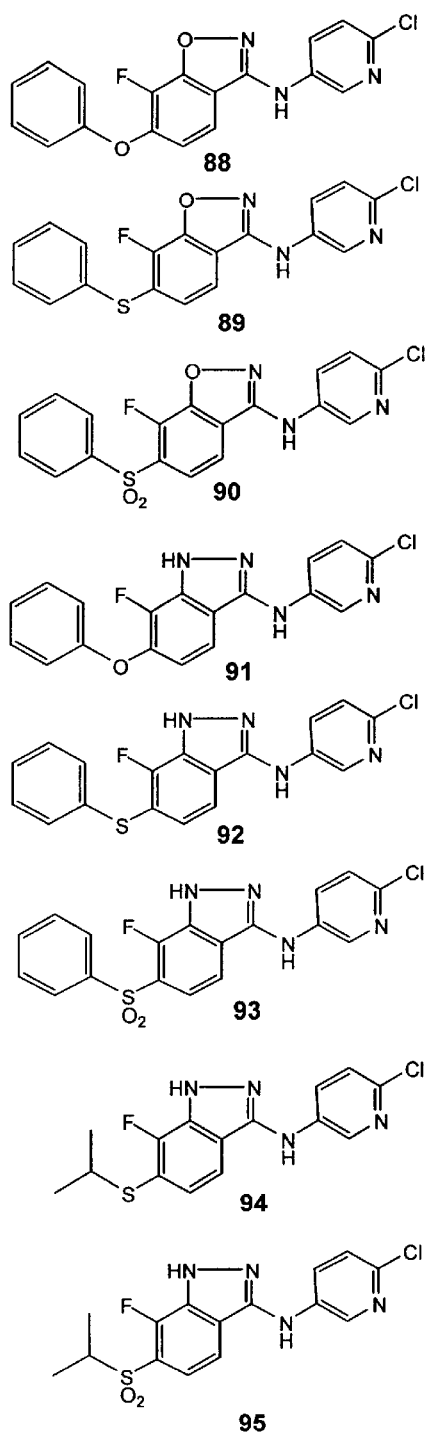
Figure 1:
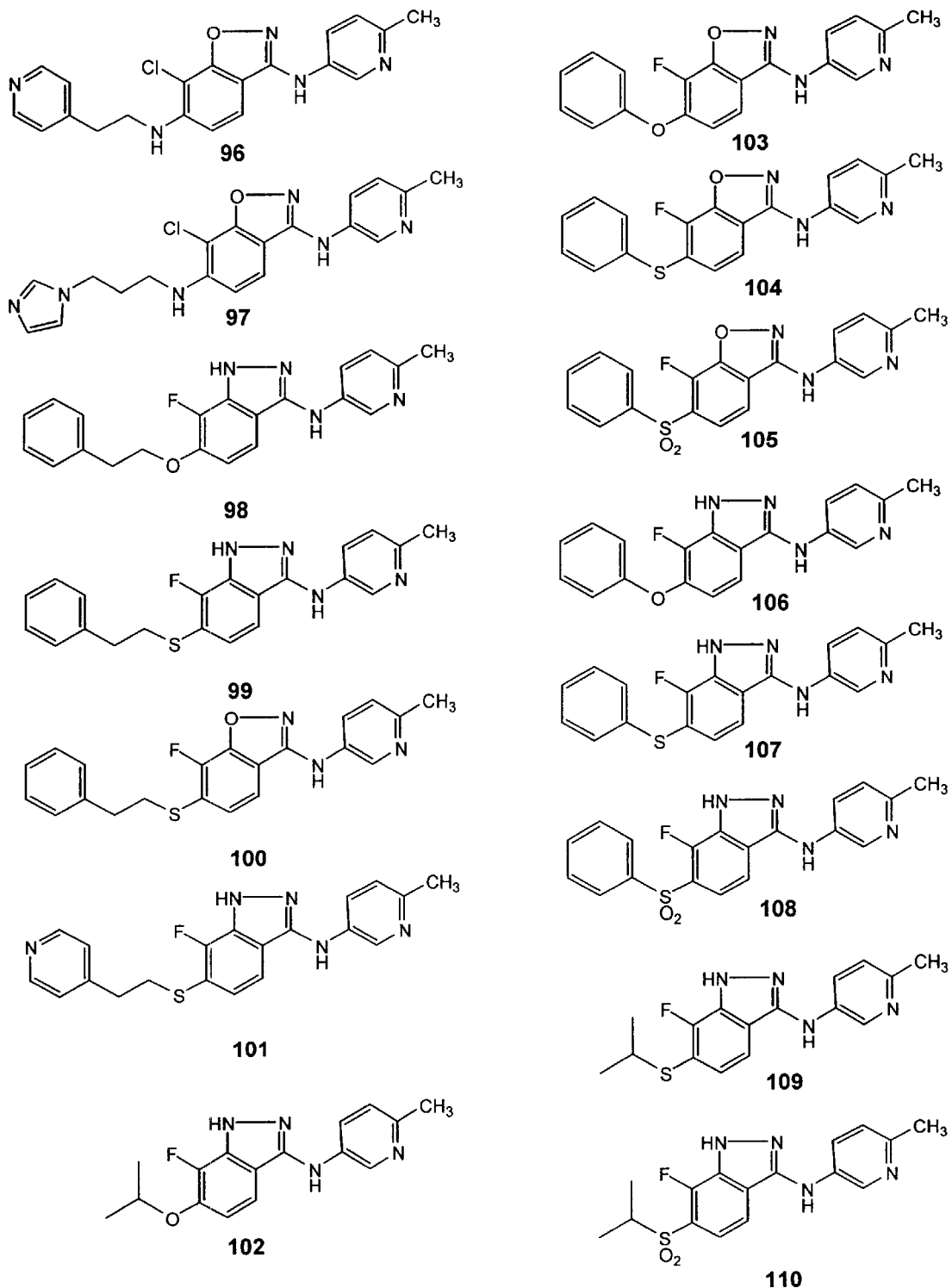
Figure 1:
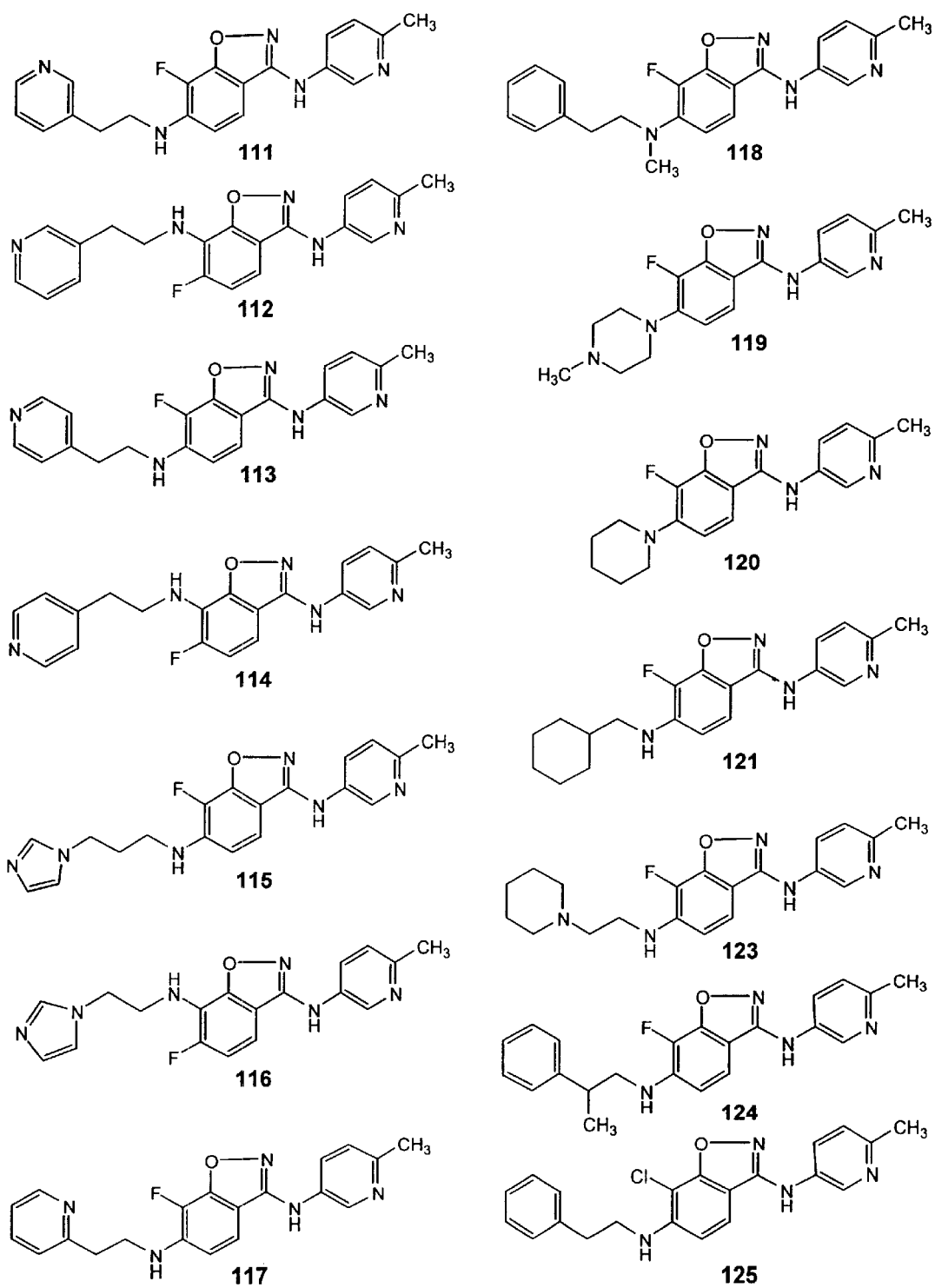
Figure 1:
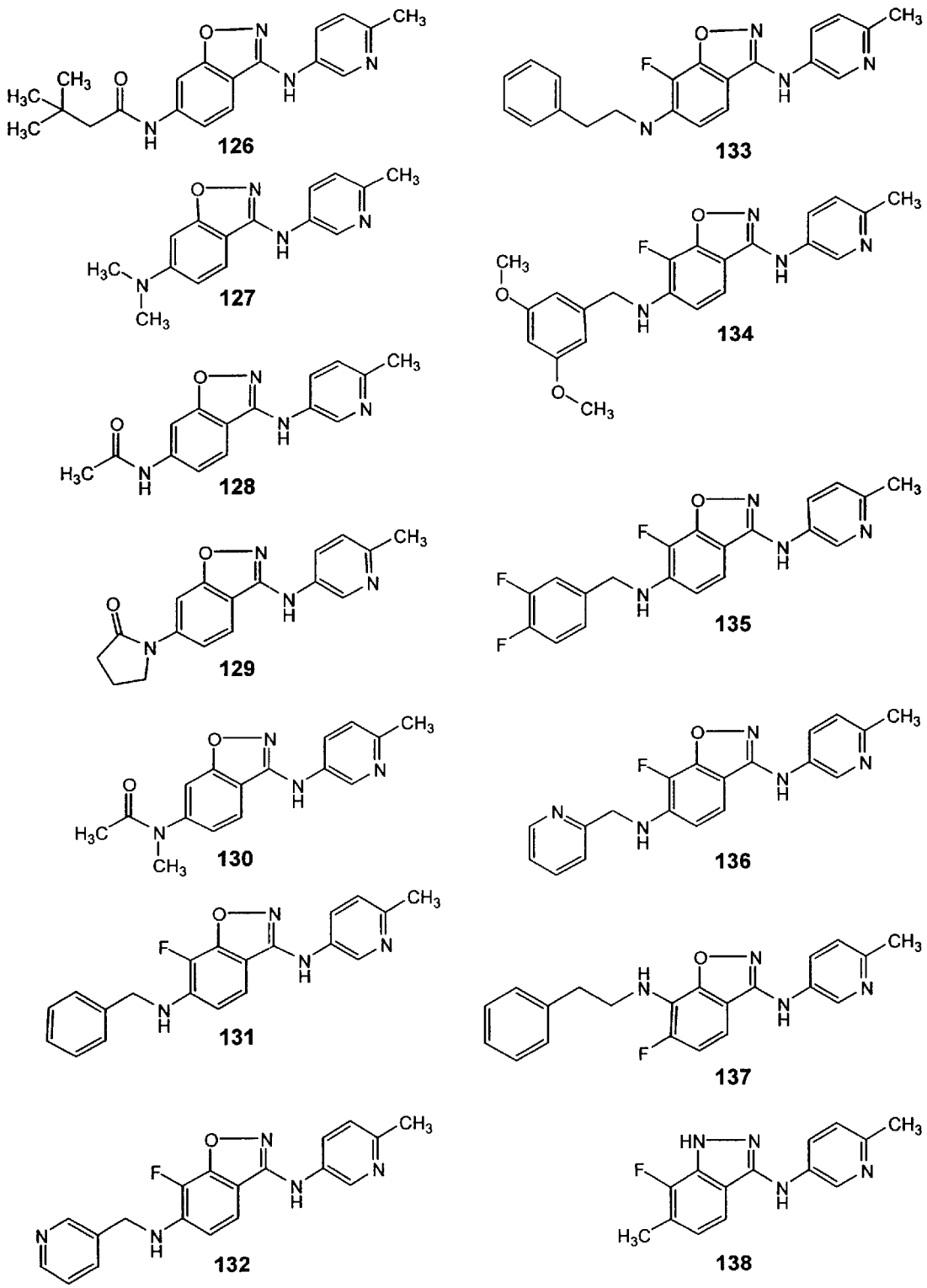
Figure 1:
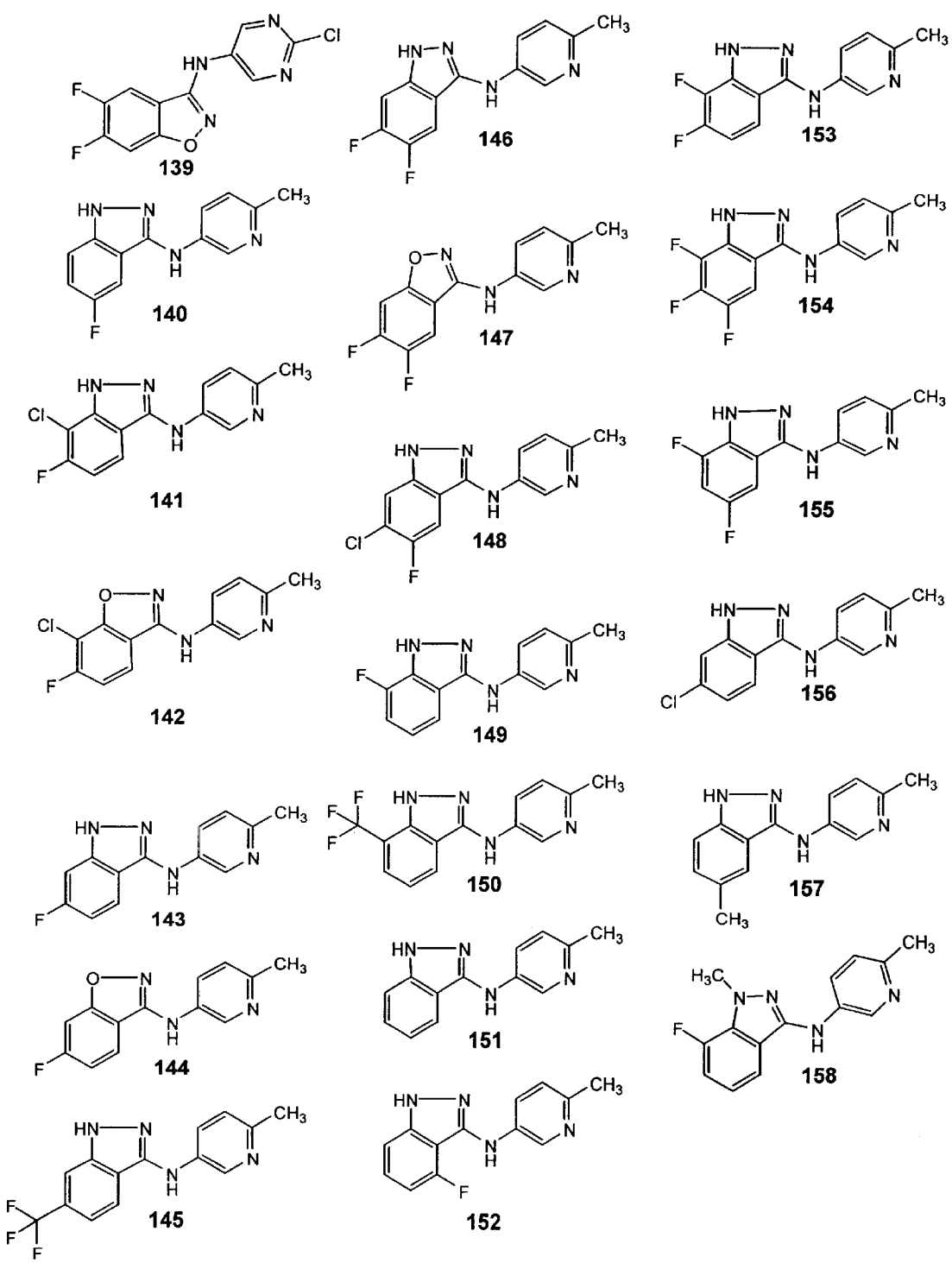
Figure 1:
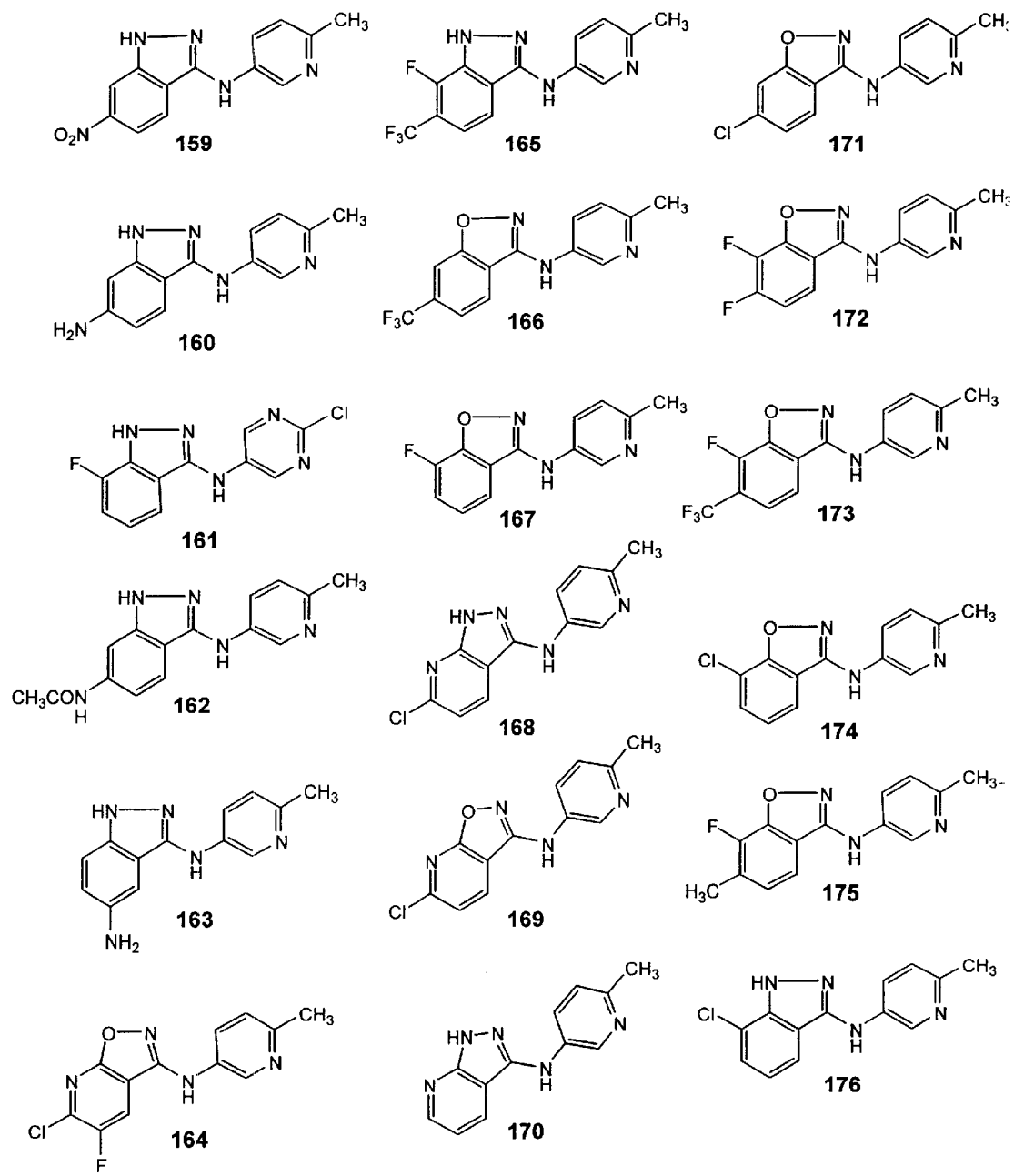

The abbreviations used herein have their conventional meaning within the chemical and biological arts. For example: CHO, Chinese hamster ovary; EBSS, Earl's Balanced Salt Solution; KCNQ, potassium channel Q; KCNQ2, potassium channel Q2, hSK, $Ca^{2+}$ activated small conductance potassium channels; SDS, sodium dodecyl sulfate; Et$_3$N, triethylamine; MeOH, methanol; and DMSO, dimethylsulfoxide.

"Compound of the invention," as used herein refers to a compound according to Formulae I or II or a combination thereof, and a pharmaceutically acceptable salt of a compound according to Formulae I or II or a combination thereof.

"Opening" and "activating" are used interchangeably herein to refer to the partial or full activation of a KCNQ channel by a compound of the invention, which leads to an increase in ion flux either into or out of a cell in which a KCNQ channel is found.

Where substituent groups are specified by their conventional chemical formulae, written from left to right, they equally encompass the chemically identical substituents which would result from writing the structure from right to left, e.g., —CH$_2$O— is intended to also recite —OCH$_2$—; —NHS(O)$_2$— is also intended to represent. —S(O)$_2$HN—, etc.

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N (CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo (C$_1$–C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g. a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', —halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O) CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', —halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R", R'" and R"" are preferably independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl) oxy-(C$_1$–C$_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The present invention provides compounds which, inter alia, are useful in the treatment of diseases through the modulation of potassium ion flux through voltage-dependent potassium channels. More particularly, the invention provides compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases), and as neuroprotective agents (e.g., to prevent stroke and the like). Compounds of the invention have use as agents for treating convulsive states, for example that following grand mal, petit mal, psychomotor epilepsy or focal seizure. The compounds of the invention are also useful in treating disease states such as gastroesophogeal reflux disorder and gastrointestinal hypomotility disorders.

Moreover, compounds of the invention are useful in the treatment of pain, for example, neuropathic pain, inflammatory pain, cancer pain, migraine pain, and musculoskeletal pain. The compounds are also useful to treat conditions, which may themselves be the origin of pain, for example, inflammatory conditions, including arthritic conditions (e.g., rheumatoid arthritis, rheumatoid spondylitis, osteoarthritis and gouty arthritis) and non-articular inflammatory conditions (e.g., herniated, ruptured and prolapsed disc syndrome, bursitis, tendonitis, tenosynovitis, fibromyalgia syndrome, and other conditions associated with ligamentous sprain and regional musculoskeletal strain). Particularly preferred compounds of the invention are less ulcerogenic than other anti-inflammatory agents (e.g., ibuprofen, naproxen and aspirin). Furthermore, the compounds of the invention are useful in treating conditions and pain associated with abnormally raised skeletal muscle tone.

The compounds of the invention are also of use in treating anxiety (e.g. anxiety disorders). Anxiety disorders are defined in the Diagnostic and Statistical Manual of Mental Disorders (Third Edition-revised 1987, published by the American Psychiatric Association, Washington, D.C., see, pages 235 to 253), as psychiatric conditions having symptoms of anxiety and avoidance behavior as characteristic features. Included amongst such disorders are generalized anxiety disorder, simple phobia and panic disorder.

Anxiety also occurs as a symptom associated with other psychiatric disorders, for example, obsessive compulsive disorder, post-traumatic stress disorder, schizophrenia, mood disorders and major depressive disorders, and with organic clinical conditions including, but not limited to, Parkinson's disease, multiple sclerosis, and other physically incapacitating disorders.

The development of therapeutic agents, which act on potassium ion channels has received considerable recent attention. One group has described a family of N-alkyl benzamides that act by blocking potassium channels (see, PCT/US98/02364, published as WO 98/37068). In contrast, the benzanilides provided herein act by opening potassium channels.

In view of the above-noted discovery, the present invention provides compounds, compositions, and methods for increasing ion flux in voltage-dependent potassium channels, particularly those channels responsible for the M-current. As used herein, the term "M-current," "channels responsible for the M-current" and the like, refers to a slowly activating, non-inactivating, slowly deactivating voltage-gated K$^+$ channel. M-current is active at voltages close to the threshold for action potential generation in a wide variety of neuronal cells, and thus, is an important regulator of neuronal excitability.

Recently, members of the voltage-dependent potassium channel family were shown to be directly involved in diseases of the central or peripheral nervous system. The benzanilides provided herein are now shown to act as potassium channel openers, particularly for KCNQ2 and KCNQ3, KCNQ4, KCNQ5 and KCNQ6 as well as the heteromultimer channels such as KCNQ2/3, KCNQ3/5 or the M-current.

DESCRIPTION OF THE EMBODIMENTS

I. Modulators of Voltage-Dependent Potassium Channels

In one aspect, the present invention provides compounds of the formula:

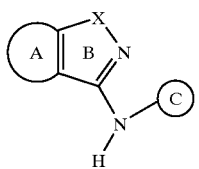

(I)

which are useful for increasing ion flow through voltage-dependent potassium channels.

In Formula I above, the ring designated by the letter A is fused to the ring designated by the letter B at two positions. Ring A is a substituted or unsubstituted aryl ring or is a five- or six-membered, substituted or unsubstituted heteroaryl ring.

The ring designated with the letter C is a heteroaromatic ring selected from the formulae:

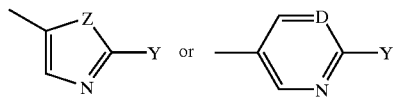

in which the letter Z represents —N(R$^o$)—, —S— or —O—, the letter D represents N or CR$^1$, and the letter Y represents halogen, R$^2$, or OR$^2$. The symbols R$^o$, R$^1$ and R$^2$ each independently represent hydrogen, substituted alkyl, or unsubstituted alkyl.

The letter Y preferably represents halogen, —CH$_3$, —OCH$_3$, or —OCF$_3$. In another preferred embodiment, the letter Y represents —F, —Cl, or —CH$_3$. Ring C is preferably a substituted or unsubstituted pyridyl ring.

The letter X represents —NR$^3$, —O—, —C(O)—, or —S(O)$_n$—, in which the letter n represents an integer from 0 to 2, preferably. The symbol R$^3$ represents hydrogen, SO$_2$R$^4$, substituted or unsubstituted alkyl, or a cycloalkyl group. The symbol R$^4$ represents hydrogen, substituted alkyl, unsubstituted allyl or cycloalkyl. Preferably, the letter X represents —O—, —S—, —C(O)— or —N(H)—. More preferably, the letter X represents —O— or —N(H)—. In those compounds of the invention in which a cycloalkyl group is present, it is preferably a C$_3$ to C$_5$ cycloalkyl group. Preferred substituted or unsubstituted alkyl groups are C$_1$ to C$_3$ alkyl groups.

In a preferred embodiment, some or all of the symbols R$^o$, R$^1$, R$^2$, R$^3$, and R$^4$ represent C$_1$–C$_4$ fluoroalkyl.

In one group of preferred embodiments, at least one member of ring A of the compound of Formula I bears a substituent, Q, which is halogen, —CN, —NO$_2$, —NR$^5$R$^6$, —NR$^5$C(O)$_q$R$^7$, —NR$^5$S(O)$_s$R$^7$, —OR$^5$, —C(O)$_t$R$^5$, —S(O)$_v$R$^7$, —R$^7$, —C(O)$_q$NR$^5$R$^6$ or —SO$_2$NR$^5$R$^6$. The symbols R$^5$ and R$^6$ each independently represent hydrogen, substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted heteroalkyl, substituted or unsubstituted heteroaryl-heteroalkyl, or substituted or unsubstituted aryl-heteroalkyl, and the symbol R$^7$ represents a substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted heteroalkyl, substituted or unsubstituted heteroaryl-heteroalkyl, or substituted or unsubstituted aryl-heteroalkyl. In this group of preferred embodiments, the letters s and v each independently represent integers from 0 to 2, and the letters q and t each independently represent integers from 1 to 2. Optionally, R$^5$ and R$^6$ or R$^5$ and R$^7$ of the substituents on ring A in this group of preferred embodiments are joined to form a ring system. Alternatively, ring A bears at least two of the substituents where the substituents are bound to adjacent members of the ring and at least two of the substituents are joined together to form at least one ring system. Most preferably, the ring system formed is a substituted or unsubstituted aryl, substituted or unsubstituted heteroaryl, substituted or unsubstituted (C$_1$–C$_7$)carbocyclyl, or substituted or unsubstituted heterocyclyl having a ring size of from 5 to 7 members.

In another group of preferred embodiments, ring A is a substituted benzo or substituted pyridyl group. More preferably, ring A is:

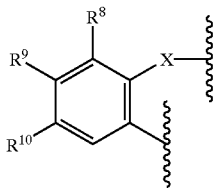

in which the symbols $R^8$, $R^9$ and $R^{10}$ each independently represent hydrogen, halogen, substituted or unsubstituted alkyl, $C(O)_pR^{11}$, $C(O)NR^{11}R^{12}$, $SO_2NR^{11}R^{12}$, $S(O)_pR^{13}$, $-OR^{13}$, or $-NR^{11}R^{12}$. The symbols $R^{11}$ and $R^{12}$ each independently represent hydrogen, substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted heteroalkyl, substituted or unsubstituted heteroaryl-heteroalkyl, or substituted or unsubstituted aryl-heteroalkyl, whereas the symbol $R^{13}$ represents a substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted heteroalkyl, substituted or unsubstituted heteroaryl-heteroalkyl, or substituted or unsubstituted aryl-heteroalkyl. In this group of preferred embodiments, the letter p represents an integer from 0 to 2. X is as discussed above, and it occupies an endocyclic position of ring B.

In an alternative group of preferred embodiments, ring A is a five- or six-membered heteroaromatic ring containing at least one substituted or unsubstituted carbon atom other than the carbon atoms at the fusion of rings A and B, and up to 2 heteroatoms, which are each, independently, —O—, —S—, —N($R^{14}$)—, or =N—, wherein the symbol $R^{14}$ represents hydrogen or a substituted or unsubstituted alkyl.

Representative compounds of the invention within the scope of Formula I are set forth in FIG. 1. Table 1 sets forth certain preferred compounds of the invention.

TABLE 1

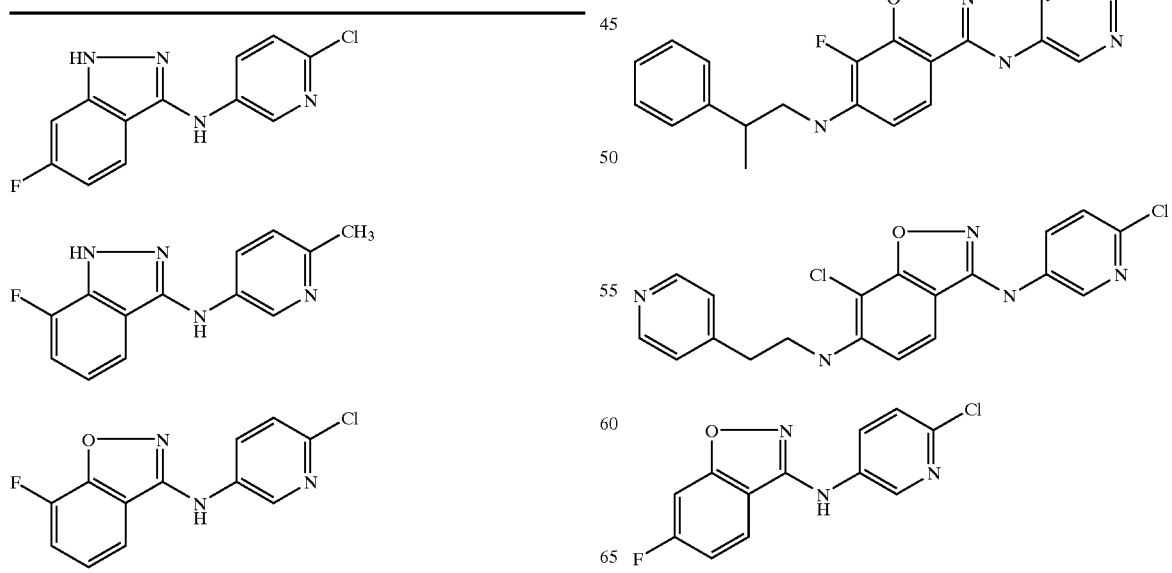

TABLE 1-continued

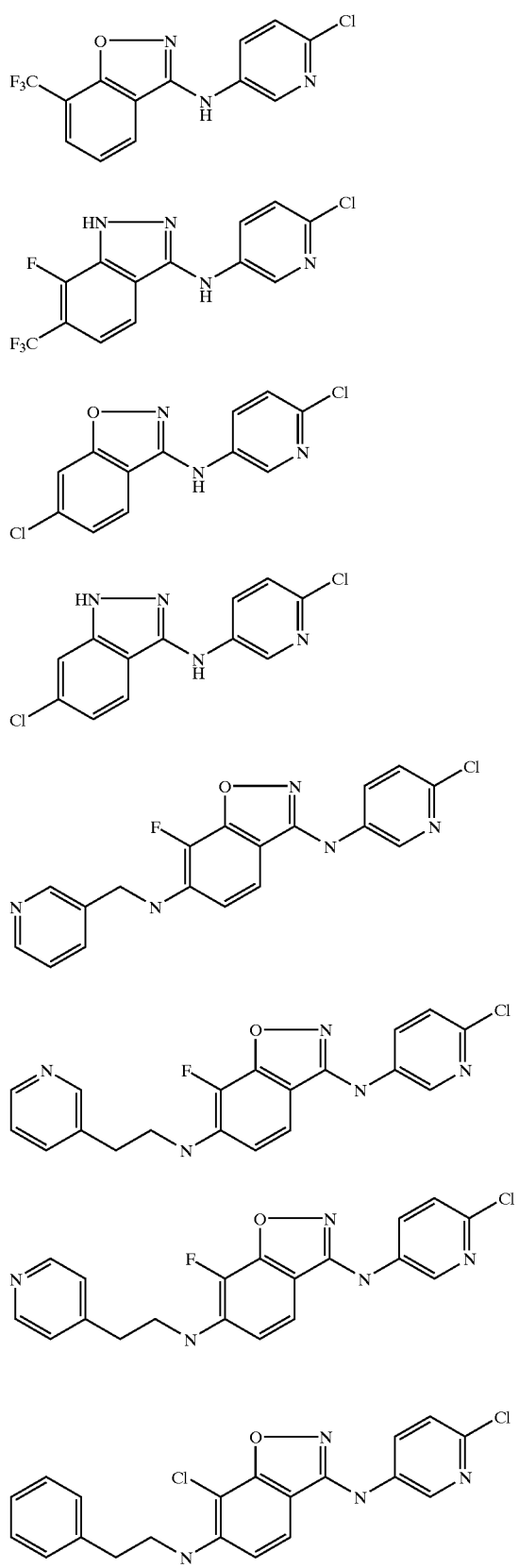

TABLE 1-continued

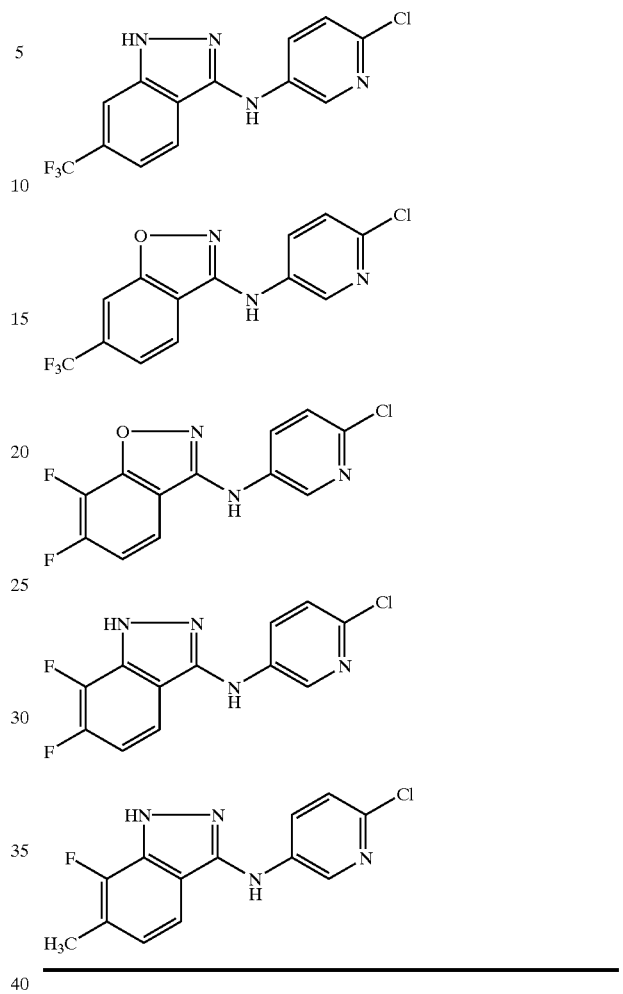

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or reactive analogues thereof are attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formula I, which are functionalized to afford compounds having a water-solubility that is enhanced relative to analogous compounds that are not similarly functionalized. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly (propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Preparation of Potassium Channel Openers

Compounds of the present invention can be prepared using readily available starting materials or known intermediates. Briefly, in one exemplary embodiment, the synthesis of the bisarylamines herein involves the acylation of a precursor of ring system C with an active acylating derivative of ring system A. The acylated adduct is converted, for example, to a hydrazone-like derivative or an N-hydroxy species, which is subsequently cyclized to form ring system B. General and specific procedures for the preparation of the present compounds are provided in the examples below.

Selected indazole-based compounds of the present invention can be prepared using standard procedures as outlined in Scheme 1, which sets forth an exemplary synthetic route. In this scheme, an aminopyridine is acylated, producing compound 1, which is converted to compound 2 by the action of hydrazine and PCl$_5$. Compound 2 is cyclized to indazole 3.

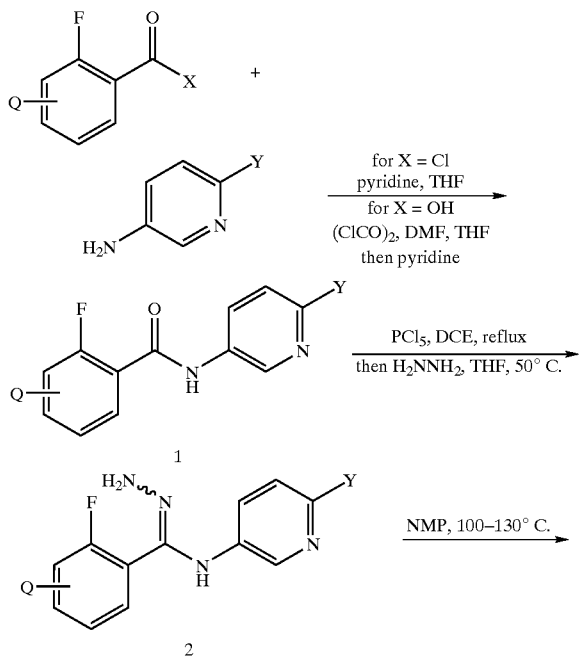

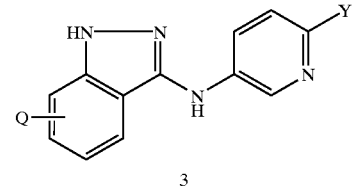

Selected benzisoxazoles of the invention are prepared according to Scheme 2, which outlines an exemplary synthetic route. Similar to the process outlined in Scheme 1, an aminopyridine is acylated to form compound 1. The carbonyl group of compound 1 is converted to an N—OH adduct, producing compound 4, which is cyclized to benzisoxazole 5.

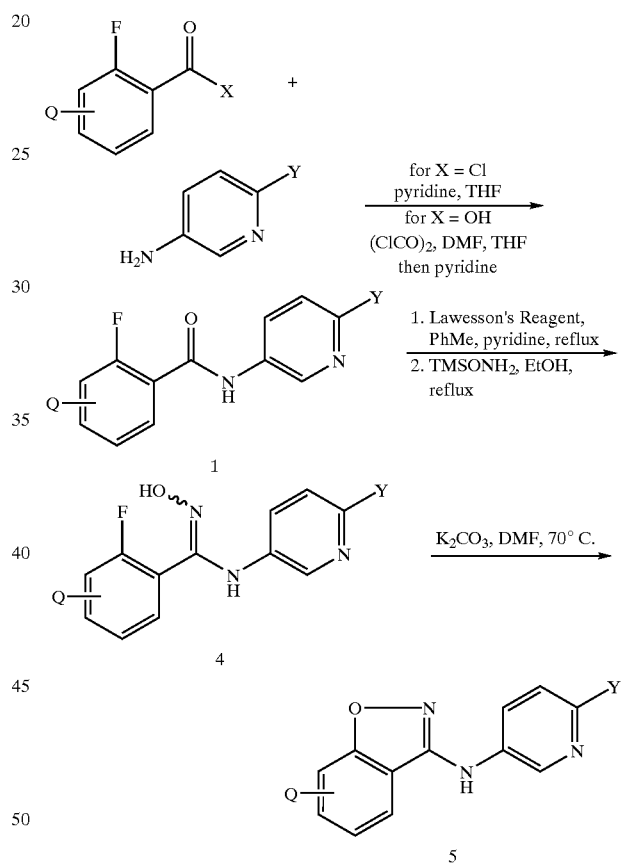

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyalent framework and a compound of the invention. If it is desired to prepare a hetereofuntionalized polyalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

II. Assays for Modulators of KCNQ Channels

Assays for determining the ability of a compound of the invention to open a potassium ion channel are generally known in the art. One of skill in the art is able to determine an appropriate assay for investigating the activity of a selected compound of the invention towards a particular ion channel. For simplicity, portions of the following discussion focuses on KCNQ2 as a representative example, however, the discussion is equally applicable to other KCNQ potassium ion channels.

KCNQ monomers as well as KCNQ alleles and polymorphic variants are subunits of potassium channels. The activity of a potassium channel comprising KCNQ subunits can be assessed using a variety of in vitro and in vivo assays, e.g. measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for inhibitors and activators of channels comprising KCNQ. Such modulators of a potassium channel are useful for treating various disorders involving potassium channels, including but not limited to, for example, central and peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety and motor neuron diseases, and can also be used as neuroprotective agents (e.g., to prevent stroke and the like). Such modulators are also useful for investigation of the channel diversity provided by KCNQ and the regulation/modulation of potassium channel activity provided by KCNQ.

Modulators of the potassium channels are tested using biologically active KCNQ, either recombinant or naturally occurring, or by using native cells, like cells from the nervous system expressing the M-current. KCNQ can be isolated, co-expressed or expressed in a cell, or expressed in a membrane derived from a cell. In such assays, KCNQ2 is expressed alone to form a homomeric potassium channel or is co-expressed with a second subunit (e.g., another KCNQ family member, preferably KCNQ3) so as to form a heteromeric potassium channel. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Activation of channels comprising KCNQ2 is achieved when the potassium channel activity value relative to the control is 130%, more preferably 150%, more preferably 170% higher. Compounds that increase the flux of ions will cause a detectable increase in the ion current density by increasing the probability of a channel comprising KCNQ2 being open, by decreasing the probability of it being closed, by increasing conductance through the channel, and increasing the number or expression of channels.

The activity of the compounds of the invention can also be represented by EC50. Preferred compounds of the invention have an EC50 in a potassium ion channel assay of from about 5 nM to about 10 $\mu$M, preferably from about 5 nM to about 1 $\mu$M, and more preferably from about 5 nM to about 500 nM.

Changes in ion flux may be assessed by determining changes in polarization (i.e., electrical potential) of the cell or membrane expressing an exemplary potassium channel such as KCNQ2, KCNQ2/3 or the M-current. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336: 1575–1595 (1997)). Whole cell currents are conveniently determined using the standard methodology (see, e.g., Hamil et al., *Pflugers. Archiv.* 391: 85 (1981). Other known assays include: radiolabeled rubidium flux assays and fluorescence assays using voltage-sensitive dyes (see, e.g., Vestergarrd-Bogind et al., *J. Membrane Biol.* 88: 67–75 (1988); Daniel et al., *J. Pharmacol. Meth.* 25: 185–193 (1991); Holevinsky et al., *J. Membrane Biology* 137: 59–70 (1994)). Assays for compounds capable of inhibiting or increasing potassium flux through the channel proteins comprising KCNQ2 or heteromultimers of KCNQ subunits can be performed by application of the compounds to a bath solution in contact with and comprising cells having a channel of the present invention (see, e.g., Blatz et al., *Nature* 323: 718–720 (1986); Park, *J. Physiol.* 481: 555–570 (1994)). Generally, the compounds to be tested are present in the range from about 1 pM to about 100 mM, preferably from about 1 pM to about 1 $\mu$M.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

Preferably, the KCNQ2 that is a part of the potassium channel used in the assay will have the sequence provided in PCT/US98/13276 or a conservatively modified variant thereof. Alternatively, the KCNQ2 of the assay will be derived from a eukaryote.

KCNQ2 orthologs will generally confer substantially similar properties on a channel comprising such KCNQ2, as described above. In a preferred embodiment, the cell placed in contact with a compound that is suspected to be a KCNQ2 homolog is assayed for increasing or decreasing ion flux in a eukaryotic cell, e.g., an oocyte of Xenopus (e.g., *Xenopus laevis*) or a mammalian cell such as a CHO or HeLa cell.

Channels that are affected by compounds in ways similar to KCNQ2 are considered homologs or orthologs of KCNQ2.

III. Pharmaceutical Compositions of Potassium Channel Openers

In another aspect, the present invention provides pharmaceutical compositions comprising a pharmaceutically acceptable excipient and a compound of Formula I provided above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I, or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat pain or anxiety, such compositions will contain an amount of active ingredient effective to achieve a clinically relevant degree of reduction in the condition being treated. Similarly, when the pharmaceutical composition is used to treat or prevent a central or peripheral nervous system disorder, e.g., Parkinson's disease a therapeutically effective amount will reduce one or more symptoms characteristic of the diseases (e.g., tremors) to below a predetermined pressure threshold. Determination of a therapeutically effective amount of a compound of the invention is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of activating or opening the KCNQ channel. In preferred embodiments, the KCNQ channel activity is at least 30% increased. Target plasma concentrations of active compound (s) that are capable of inducing at least about 50%, 70%, or even 90% or higher activation of the KCNQ channel potassium flux are presently preferred. The percentage of activation of the KCNQ channel in the patient can be monitored to assess the appropriateness of the plasma drug concentration achieved, and the dosage can be adjusted upwards or downwards to achieve the desired percentage of activation.

As is well known in the art, therapeutically effective amounts for use in humans can also be determined from animal models. For example, a dose for humans can be formulated to achieve a circulating concentration that has been found to be effective in animals. A particularly useful animal model for predicting anticonvulsant dosages is the maximal electroshock assay (Fischer R S, *Brain Res. Rev.* 14: 245–278 (1989)). The dosage in humans can be adjusted by monitoring KCNQ channel activation and adjusting the dosage upwards or downwards, as described above.

A therapeutically effective dose can also be determined from human data for compounds which are known to exhibit similar pharmacological activities, such as retigabine (Rudnfeldt et al., *Neuroscience Lett.* 282: 73–76 (2000)).

Adjusting the dose to achieve maximal efficacy in humans based on the methods described above and other methods as are well-known in the art is well within the capabilities of the ordinarily skilled artisan.

By way of example, when a compound of the invention is used in the prophylaxis and/or treatment of an exemplary disease such as epilepsy, a circulating concentration of administered compound of about 0.001 $\mu$M to 20 $\mu$M is considered to be effective, with about 0.01 $\mu$M to 5 $\mu$M being preferred.

Patient doses for oral administration of the compounds described herein, which is the preferred mode of administration for prophylaxis and for treatment of an exemplary disease such as epilepsy, typically range from about 1 mg/day to about 10,000 mg/day, more typically from about 10 mg/day to about 1,000 mg/day, and most typically from about 1 mg/day to about 500 mg/day. Stated in terms of patient body weight, typical dosages range from about 0.01 to about 150 mg/kg/day, more typically from about 0.1 to about 15 mg/kg/day, and most typically from about 0.5 to about 10 mg/kg/day.

For other modes of administration, dosage amount and interval can be adjusted individually to provide plasma levels of the administered compound effective for the particular clinical indication being treated. For example, if acute epileptic seizures are the most dominant clinical manifestation, in one embodiment, a compound according to the invention can be administered in relatively high concentrations multiple times per day. Alternatively, if the patient exhibits only periodic epileptic seizures on an infrequent, periodic or irregular basis, in one embodiment, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Compound Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p.1, 1975. The exact formulation, route of administration and dosage can be chosen by the individual physician in view of the patient's condition and the particular method in which the compound is used.

IV. Methods for Increasing Ion Flow in Voltage-dependent Potassium Channels

In yet another aspect, the present invention provides methods for increasing ion flow through voltage dependent potassium channels in a cell. The method includes contacting a cell containing the target ion channels with an amount of a compound according to Formula I sufficient to open a potassium channel.

The methods provided in this aspect of the invention are useful for the diagnosis of conditions that can be treated by modulating ion flux through voltage-dependent potassium channels, or for determining if a patient will be responsive to therapeutic agents, which act by opening potassium channels. In particular, a patient's cell sample can be obtained and contacted with a compound of Formula I above and the ion flux can be measured relative to a cell's ion flux in the absence of a compound of Formula I. An increase in ion flux will typically indicate that the patient will be responsive to a therapeutic regimen of ion channel openers.

V. Methods for Treating Conditions Mediated by Voltage-dependent Potassium Channels In still another aspect, the present invention provides a method for the treatment of a central or peripheral nervous system disorder or condition through modulation of a voltage-dependent potassium channel. In this method, a subject in need of such treatment is administered an effective amount of a compound having the formula provided above.

The compounds provided herein are useful as potassium channel openers and find therapeutic utility via modulation of voltage-dependent potassium channels in the treatment of diseases or conditions. The potassium channels that are typically opened are described herein as voltage-dependent potassium channels such as the KCNQ potassium channels. As noted above, these channels may include homomultimers and heteromultimers of KCNQ2, KCNQ3, KCNQ4, KCNQ5 and KCNQ6. A heteromultimer of two proteins, e.g., KCNQ2 and KCNQ3 is referred to as, for example, KCNQ2/3, KCNQ3/5, etc. The conditions that can be treated with the compounds and compositions of the present invention may include, but are not limited to, central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, Alzheimer's disease, age-related memory loss, learning deficiencies, anxiety, and motor neuron diseases). The compounds and compositions of the present invention may also serve as neuroprotective agents (e.g., to prevent stroke and the like). In a preferred embodiment, the condition or disorder to be treated is epilepsy or seizures. In another preferred embodiment, the condition or disorder is hearing loss.

In therapeutic use for the treatment of epilepsy or other neurological conditions, the compounds utilized in the pharmaceutical method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

EXAMPLES

The following examples are offered to illustrate, but not to limit the claimed invention.

In the examples below, unless otherwise stated, temperatures are given in degrees Celsius (° C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

Example 1

Preparation of 2-substituted-5-aminopyridines
1.1 Reduction of Nitropyridines

Referring to Scheme 3, aminopyridine starting materials (II) are prepared by reducing the corresponding nitropyridines (I). One skilled in the art will recognize that there are several methods to accomplish step 1. Tin chloride in DMF, hydrogenation using catalytic palladium and sodium borohydride in the presence of catalytic nickel chloride are known exemplary methods.

Scheme 3

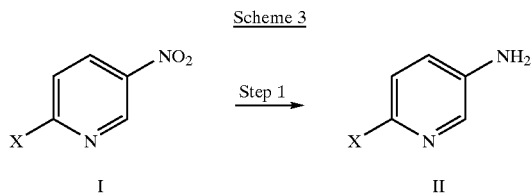

1.1a Synthesis of 5-amino-2-bromopyridine

Tin (II) chloride hydrate (0.78 g, 3.5 mmol) was added to a stirring solution of 5-nitro-2-bromopyridine (0.24 g, 1.2 mmol) in DMF (5 mL) at RT. After 2 h, 6N NaOH (2 mL) was added and the suspension was stirred vigorously for 10 min. The organics were extracted with diethyl ether (2×10 mL), washed with brine (2×10 mL) and dried (Na$_2$SO$_4$). The filtered solution was then concentrated under reduced pressure to afford the desired product as a yellow oil (0.178 g, 86%), which was used without further purification.
1.2 Rearrangement of Nicotinic Acids Aminopyridines are prepared by rearrangement of the corresponding nicotinic acids (III) (Scheme 4) using a modified Schmidt reaction, followed by deprotection of the aniline group generated the desired aminopyridines (IV) as the corresponding TFA salts.

Scheme 4

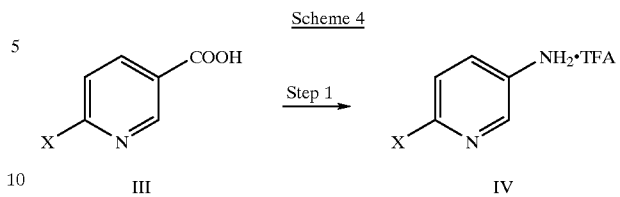

1.2 a Synthesis of 5-amino-2-methylpyridine (TFA Salt)

A solution of diphenylphosphorylazide (430 μL, 2 mmol), triethylamine (278 μL, 2 mmol) and 6-methyl-nicotinic acid (274 mg, 2 mmol) in t-butanol (30 mL) was heated at reflux for 4 h. The solution was cooled to RT and poured into water (50 mL). The organics were extracted with ether (3×20 mL), washed with brine (2×10 mL) and dried (Na$_2$SO$_4$). Column chromatography (1:1 hexane/ethyl acetate) of the boc-protected aminopyridine gave the intermediate as a white solid (156 mg, 38%).

The desired 5-amino-2-methylpyridine-TFA salt was generated in situ by stirring in a 20% TFA/DCM solution (2 mL) for 4 h. The solution was concentrated under reduced pressure to afford a semi-solid, which was used without further purification.
1.2 b Synthesis of 5-amino-2-(trifluoromethyal)pyridine (TFA Salt)

A solution of diphenylphosphorylazide (644 μL, 3 mmol), triethylamine (417 μL, 3 mmol) and 6-(trifluoromethyl)-nicotinic acid (573 mg, 3 mmol) in t-butanol (50 mL) was heated at reflux for 4 h, then cooled to RT and poured into water (50 mL). The organics were extracted with ether (3×20 mL), washed with brine (2×10 mL) and dried (Na$_2$SO$_4$). Column chromatography (1:1 hexane/ethyl acetate) of the boc-protected aniline gave the intermediate as a white solid (389 mg, 50%).

The desired 5-amino-2-methylpyridine-TFA salt was generated in situ by stirring in a 20% TFA/DCM solution (2 mL) for 4 h. The solution was concentrated under reduced pressure to afford a semi-solid, which was used without further purification.
1.3: Displacement of 2-halopyridines.

Several aminopyridines, which are not readily accessible via the methods outlined in Schemes 3 or 4, may be synthesized via nucleophilic displacement of 2-chloropyridines as depicted in Scheme 5.

Scheme 5

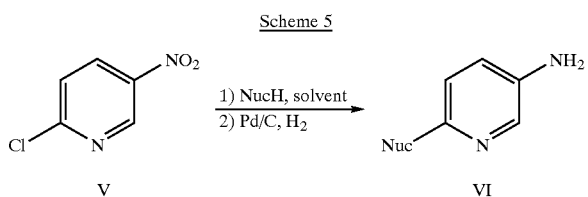

1.3a Synthesis of 5-amino-2-fluoropyridine

A mixture of 5-nitro-2-chloropyridine (2.0 g, 12.6 mmol) and anhydrous potassium fluoride (2.2 g, 38 mmol) in a combination of sulfalone (6 mL) and benzene (4 mL) was stirred at RT for 20 min. The benzene was then removed by distillation. The resulting mixture was heated at 150° C. for 12 h. The mixture was cooled to RT whereupon water (60 mL) was added. The desired product was separated from the solution via steam distillation. Extraction of the distillate with diethyl ether (2×10 mL) followed by drying (Na$_2$SO$_4$)

and concentration gave 5-nitro-2-fluoropyridine as a water white oil (1.3 g, 73%).

10% Palladium on charcoal (20 mg, cat) was added to a stirring solution of 5-nitro-2-fluoropyridine (100 mg, 0.7 mmol) in dichloromethane (3 mL) at RT. 1 atmosphere of hydrogen gas was then applied to the solution and the mixture was stirred at RT for 1 h. The mixture was passed through a short plug of celite and the resulting solution, containing the desired 5-amino-2-fluoropyridine, was used without further purification.

Example 2

2.1 Synthesis of Bisarylamines from Substituted Aminopyridines 1.2a General Method for Synthesis of 1, When X=Cl An aniline (1.55 mmol) was dissolved in dry THF (5 mL) and treated with pyridine (0.075 mL, 0.6 equivalents) followed by a 2-fluorobenzoyl chloride (1.1 equivalents; slow addition; a precipitate formed immediately). After 2 h, saturated $NaHCO_3$ solution (15 mL) was added. After 30 min of vigorous stirring, the mixture was diluted with EtOAc (15 mL). The organic layer was washed with water (1×5 mL), dried ($Na_2SO_4$) and filtered. Removal of the solvent provides the products 1 as solids, typically in high yields (>95%) and with high purity (typically >95% by LC/MS).

1.3a General Method for Synthesis of 1, When X=OH

A 2-fluorobenzoic acid (1.7 mmol, 1.1 equivalents) was dissolved in dry THF (5 mL) and treated with dry DMF (3 drops) followed by oxalyl chloride (1.3 equivalents; slow addition; gas evolution; mild exotherm). After 1 h, an aniline (1.55 mmol) was added (a precipitate forms immediately) and 2 h later, saturated $NaHCO_3$ solution (15 mL) was added. After 30 min of vigorous stirring, the mixture was diluted with EtOAc (15 mL). The organic layer was washed with water (1×5 mL) and silica gel (2 g) was added. Removal of the solvent provided a solid, which was applied to a column of silica gel (1"×6") and eluted with EtOAc/hexanes. The products 1 were typically obtained as solids in good yields (>70%) and with high purity (>95% by LC/MS).

Example 3

3.1 General Method for Synthesis of Compound 2

Example 3 describes a general method for preparing compound 2. Compound 1 (0.40 mmol) and $PCl_5$ (1.2 equivalents) were heated at reflux in dry 1,2-dichloroethane (2 mL) for 1 h. The mixture was brought to 50° C., diluted with dry THF (2 mL) and treated with hydrazine (15 equivalents). After 1 h, most of the solvent was removed and the resulting mixture was diluted with $CHCl_3$ (4 mL), brine (2 mL), 6 N NaOH (0.4 mL), and saturated $NaHCO_3$ solution. The resulting mixture was stirred for 20 min and then the aqueous layer was extracted with 15% i-PrOH/$CHCl_3$ (3×2 mL). The organic layers were combined, silica gel (1 g) was added and the solvent was removed. The resulting solid was applied to a column of silica gel (0.5 in×6 in) and eluted with MeCN/hexanes/$CH_2Cl_2$. The products 2 were typically obtained in good yields (>90%/o) and with good purity (>90% by LC/MS).

Example 4

4.1 General Method for Synthesis of Compound 3

Example 4 sets forth a general method for preparing compound 3. Compound 2 (0.4 mmol) was dissolved in dry NMP (2 mL) and heated at 100–130° C. for 1 h. After cooling to room temperature, the mixture was diluted with EtOAc (10 mL), brine (4 mL), and saturated $NaHCO_3$ solution (2 mL). The organic layer was washed with brine (2×2 mL). Silica gel (600 mg) was added, and the solvent was removed. The resulting solid was applied to a column of silica gel (0.5 in×8 in) and eluted with EtOAc/hexanes. The products 3 were typically obtained as solids in high yields (>90%) and with high purities (>95% by LC/MS).

Example 5

5.1 General Method for Synthesis of Compound 4

Example 5 sets forth a general method for preparing compound 4. Compound 1 (0.5 mmol) and Lawesson's reagent (1.3 equivalents) were heated at reflux in 10% pyridine/toluene (2 mL) for 2 h (solution turned yellow). The mixture was brought to room temperature and diluted with water (1 mL), EtOAc (5 mL) and saturated $NaHCO_3$ solution (2 mL). After stirring vigorously for 30 min, the organic layer was washed with water (1×2 mL), dried ($Na_2SO_4$) and filtered. Removal of the solvent provided a yellow solid, which was heated at reflux with $TMSONH_2$ (3 equivalents) in EtOH (1 mL) for 2 h. The mixture was brought to room temperature and diluted with water (1 mL), EtOAc (5 mL) and saturated $NaHCO_3$ solution (4 mL). The organic layer was washed with water (1×1 mL) and silica gel (800 mg) was added. Removal of the solvent provided a solid, which was applied to a column of silica gel (0.5 in×6 in) and eluted with EtOAc/hexanes. The products 4 were typically obtained as solids in high yields (>90%) and with high purity (>95% by LC/MS).

Example 6

6.1 General Method for Synthesizing Compound 5

Example 6 provides a general method for the preparation of compound 6. Compound 4 (0.4 mmol) was dissolved in dry DMF (1.2 mL) and heated at 70° C. with $K_2CO_3$ (3 equivalents) for 15 h. The mixture was diluted with water (1 ML), EtOAc (4 mL) and brine (3 mL). The organic layer was washed with brine (2×2 mL) and silica gel (1 g) was added. Removal of the solvent provides a solid, which was applied to a column of silica gel (0.5 in×8 in) and eluted with EtOAc/hexanes/$CH_2Cl_2$. The products 5 were typically obtained as solids in good yields (>80%) and with high purity (>95% by LC/MS).

Example 7

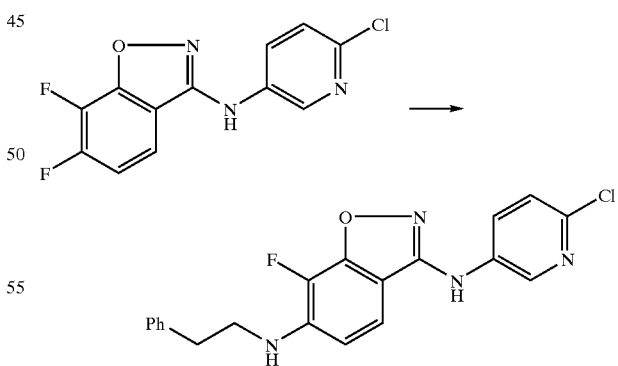

7.1 General Method for Elaborating the Heterocyclic Ring

Example 7 sets forth method generally applicable to the elaboration of the heterocyclic ring portion of compounds of the invention. By way of example, the method is used to prepare 3-(4-chloropyridin-3-yl)amino-7-fluoro-6-(2-phenethylamine)benzisoxazole.

The starting material (30 mg, 0.11 mmol) and phenethylamine (5 equivalents) were dissolved in dry DMSO (0.5 mL) and heated at 125–130° C. for 20 h. Water (0.5 mL), brine (3 mL) and EtOAc (5 mL) were added. The organic layer was washed with brine (2×1 mL) and then silica gel (400 mg) was added. Removal of the solvent left a solid which was applied to a column of silica gel (0.5 in×6 in) and eluted with 30–50% EtOAc/hexanes. Removal of the solvent provided the product (24 mg, 57%) as a solid. $^1$H NMR (CDCl$_3$, CD$_3$OD) δ 8.33 (d, J=2.8 Hz, 1H), 8.17 (dd, J=3.0, 8.9 Hz, 1H), 7.37 (d, J=8.7 Hz, 1H), 7.10–7.32 (m, 6H), 6.64 (dd, J=6.6, 8.5 Hz, 1H), 3.39 (t, J=7.1 Hz, 2H), 2.85 (t, J=7.0 Hz, 2H); MS(ESI): 383 (MH$^+$).

Example 8

Example 8 provides structures and the results of characterization for representative compounds of the invention prepared by the methods set forth above.

8.1 3-(4-Chloropyridin-3-yl)amino-6-trifluoromethylindazole

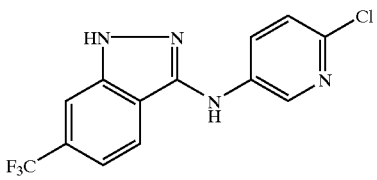

$^1$H NMR (CDCl$_3$, CD$_3$OD) δ 8.38 (s, 1H), 8.06 (d, J=6.6 Hz, 1H), 7.82 (d, J=8.3 Hz, 1H), 7.62 (s, 1H), 7.22 (d, J=8.9 Hz, 1H), 7.17 (d, J=8.7 Hz, 1H); MS(ESI): 313 (MH$^+$).

8.2 3-(4-Chloropyridin-3-yl)amino-7-fluoro-6-trifluoromethylindazole

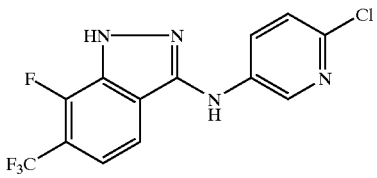

$^1$H NMR (CDCl$_3$, CD$_3$OD) δ 8.39 (d, J=2.8 Hz, 1H), 8.04 (dd, J=3.0, 8.9 Hz, 1H), 7.56 (d, J=8.4 Hz, 1H), 7.13 (d, J=8.7 Hz, 1H), 7.08 (dd, J=5.7, 8.3 Hz, 1H); MS(ESI): 331 (MH$^+$).

8.3 3-(4-Chloropyridin-3-yl)amino-7-fluoro-6-methylbenzisoxazole

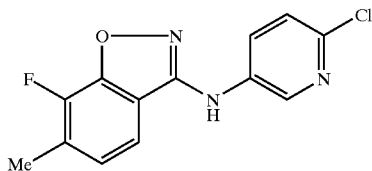

$^1$HNMR (CDCl$_3$, CD$_3$OD) δ 8.37 (d, J=2.9 Hz, 1H), 8.20 (dd, J=3.0, 8.9 Hz, 1H) 7.43 (d, J=8.0 Hz, 1H), 7.22 (d, J=8.8 Hz, 1H), 6.98 (dd, J=5.7, 8.0 Hz, 1H), 2.31 (d, J=2.4 Hz, 3H); MS(ESI): 278 (MH$^+$).

8.4 3-(4-Chloropyridin-3-yl)amino-7-chlorobenzisoxazole

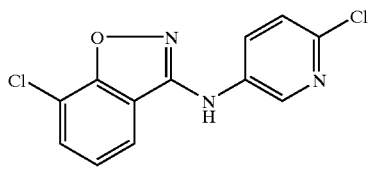

$^1$H NMR (CDCl$_3$, CD$_3$OD) δ 8.39 (d, J=2.8 Hz, 1H), 8.16 (dd, J=2.8, 8.7 Hz, 1H), 7.70 (d, J=8.0 Hz, 1H), 7.40 (d, J=7.5 Hz, 1H), 7.20 (d, J=8.7 Hz, 1H), 7.11 (dd, J=7.8, 7.8 Hz, 1H); MS(ESI): 281 (MH$^+$).

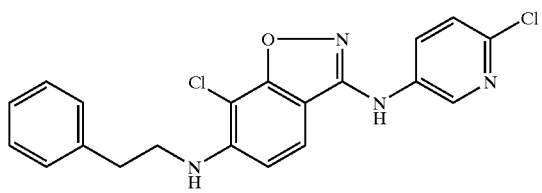

8.5 3-(4-Chloropyridin-3-yl)amino-7-chloro-6-(2-phenethylamine)-benzisoxazole (80)

$^1$H NMR (CDCl$_3$, CD$_3$OD) δ 8.32 (d, J=2.8 Hz, 1H), 8.28 (dd, J=3.0, 8.7 Hz, 1H), 7.52 (d, J=8.7 Hz, 1H), 7.18–7.30 (m, 6H), 6.66 (d, J=7.9 Hz, 1H), 3.50 (t, J=7.1 Hz, 2H), 2.94 (t, J=7.0 Hz, 2H); MS(ESI): 399 (MH$^+$).

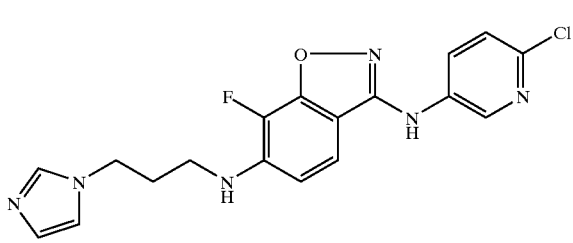

8.6 3-(4-Chloropyridin-3-yl)amino-7-fluoro-6-(3-(1-imidazyl)propylamine)-benzisoxazole (71)

$^1$H NMR (CDCl$_3$, CD$_3$OD) δ 8.35 (d, J=2.8 Hz, 1H), 8.22 (dd, J=2.9, 8.9 Hz, 1H), 7.42 (s, 1H), 7.37 (d, J=8.7 Hz, 1H), 7.23 (d, J=9 Hz, 1H), 6.96 (s, 1H), 6.90 (s, 1H), 6.47 (dd, J=1.9, 8.5 Hz, 1H), 4.05 (t, J=6.6 Hz, 2H), 3.15 (t, J=6.6 Hz, 2H), 2.07 (tt, J=6.6, 6.6 Hz, 2H); MS(ESI): 387 (MH$^+$).

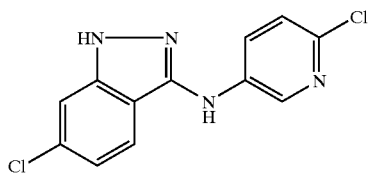

8.7 3-(4-Chloropyridin-3-yl)amino-6-chloroindazole (19)

$^1$H NMR (CDCl$_3$, CD$_3$OD) δ 8.32 (s, 1H), 7.98 (d, J=8.7 Hz, 1H), 7.58 (d, J=8.6 Hz, 1H), 7.26 (s, 1H), 7.11 (d, J=8.7 Hz, 1H), 6.91 (d, J=8.6 Hz, 1H); MS(ESI): 279 (MH$^+$).

Example 9

This example illustrates a KCNQ2 screening protocol for evaluating compounds of the present invention. The assay set forth herein measures the activity of a KCNQ potassium channel in terms of ion efflux.

Cells expressing voltage-gated K$^+$ channels, such as KCNQ2-like channels were loaded with $^{86}$Rb$^+$ by culture in media containing $^{86}$RbCl. Following loading, culture media was removed and the cells were washed in EBSS to remove residual traces of $^{86}$Rb$^+$. Cells were preincubated with drug (0.01–30 μM in EBSS) and then $^{86}$Rb$^+$ efflux was stimulated by exposing cells to EBSS solution supplemented with a sub-maximal concentration of KCl (generally 7–20 mM) in the continued presence of drug. After a suitable efflux period, the EBSS/KCl solution was removed from the cells and the $^{86}$Rb$^+$ content determined by Cherenkov counting (Wallac Trilux). Cells were then lysed with a SDS solution and the $^{86}$Rb$^+$ content of the lysate determined. Percent $^{86}$Rb$^+$ efflux was calculated according to:

($^{86}$Rb$^+$ content in EBSS/($^{86}$Rb$^+$ content in EBSS+$^{86}$Rb$^+$ content of the lysate))*100

Efflux was normalized to the maximal $^{86}$Rb$^+$ efflux (i.e., that induced by a high concentration of KCl, generally 30–135 mM).

Compounds of the invention (FIG. 1) were prepared according to the general methods set forth in the examples and they were assayed using the above-described method. The EC50 values for representative compounds of the invention typically ranged from about 5 nM to about 10 μM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the structure:

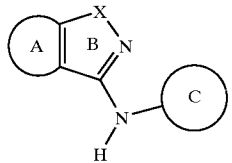

wherein,
ring A is fused to ring B and is a member selected from substituted or unsubstituted aryl groups, and five- and six-membered, substituted or unsubstituted heteroaryl rings;
ring C is a heteroaromatic ring, which is a member selected from the group consisting of:

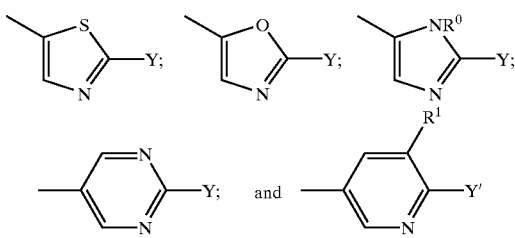

wherein,
Y is a member selected from the group consisting of halogen, R$^2$, and OR$^2$;
R$^o$, R$^1$ and R$^2$ are members independently selected from the group consisting of H and substituted or unsubstituted alkyl;
Y' is a member selected from the group consisting of halogen, R$^{2'}$, and OR$^{2'}$;

R$^{2'}$ is substituted or unsubstituted alkyl;
X is a member selected from the group consisting of —NR$^3$, —O—, and —S—; and
R$^3$ is a member selected from the group consisting of H, SO$_2$R$^4$, substituted or unsubstituted alkyl and substituted or unsubstituted cycloalkyl, wherein R$^4$ is a member selected from the group consisting of substituted or unsubstituted alkyl and substituted or unsubstituted cycloalkyl.

2. The compound according to claim 1, wherein at least one member of said ring A bears a substituent bound thereto that is a member selected from the group consisting of halogen, —CN, —NO$_2$, —NR$^5$R$^6$, —NR$^5$C(O)$_q$R$^7$, —NR$^5$S(O)$_q$R$^7$, —OR$^5$, —C(O)$_2$R$^5$, —C(O)R$^7$, —S(O)$_s$R$^7$, —R$^5$, —C(O)$_q$NR$^5$R$^6$ and —SO$_2$NR$^5$R$^6$;

R$^5$ and R$^6$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;

R$^7$ is a member selected from the group consisting of substituted or unsubstituted alkyl, substituted or unsubstituted cycloalkyl, substituted or unsubstituted aryl, substituted or unsubstituted heteroaryl, substituted or unsubstituted aralkyl, substituted or unsubstituted heterocyclyl, substituted or unsubstituted heteroalkyl, substituted or unsubstituted heteroaryl-heteroalkyl, and substituted or unsubstituted aryl-heteroalkyl;

s is a member selected from the group consisting of the integers from 0 to 2; and
q is a member selected from the group consisting of the integers from 1 to 2.

3. The compound according to claim 2, wherein R$^5$ and a member selected from the group consisting of R$^6$ and R$^7$ of said substituent are joined to form a ring system.

4. The compound according to claim 2, wherein said ring A bears at least two of said substituents, wherein said substituents are bound to adjacent members of said ring A and at least two of said substituents are joined together to form at least one ring system.

5. The compound according to claim 4, wherein said at least one ring system is a member selected from the group consisting of substituted or unsubstituted (C$_1$–C$_7$) carbocyclyl, and substituted or unsubstituted heterocyclyl having a ring size of from 5 to 7 members.

6. The compound according to claim 1, wherein ring C is a pyridyl ring.

7. The compound according to claim 1, wherein Y is a member selected from the group consisting of H, halogen, CH$_3$, OCH$_3$, CF$_3$ and OCF$_3$.

8. The compound according to claim 7, wherein Y is a member selected from the group consisting of F, Cl, and CH$_3$.

9. The compound according to claim 1, wherein X is a member selected from the group consisting of —O—, —S—, and —N(H)—.

10. The compound according to claim 9, wherein Y is a member selected from the group consisting of H, halogen, CH$_3$, OCH$_3$, CF$_3$ and OCF$_3$.

11. The compound according to claim 10, wherein Y is a member selected from the group consisting of F, Cl, and CH$_3$.

12. The compound according to claim 1, wherein ring A is a five- or six-membered heteroaromatic ring containing at least one substituted or unsubstituted carbon atom other than the carbon atoms at the fusion of rings A and B, and up to 2 heteroatoms, which are members independently selected from the group consisting of —O—, —S—, and —N(R$^{14}$)—, and =N—; and R$^{14}$ is a member selected from the group consisting of H and substituted or unsubstituted alkyl.

13. The compound according to claim 1, wherein said ring A is a member selected from the group consisting of substituted benzo and substituted pyridyl groups.

14. The compound according to claim 13, wherein ring A is:

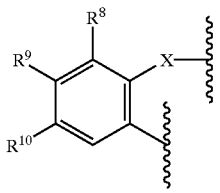

wherein,
R$^8$, R$^9$ and R$^{10}$ are members independently selected from the group consisting of H, halogen, substituted or unsubstituted alkyl, C(O)$_b$R$^{11}$, C(O)NR$^{11}$R$^{12}$, SO$_2$NR$^{11}$R$^{12}$, NR$^{12}$R$^{13}$, S(O)$_d$R$^{13}$, OR$^{13}$, NHR$^{13}$, CN, and fluoroalkyl wherein, R$^{11}$ and R$^{12}$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl, and R$^{11}$ and R$^{12}$ are optionally joined together with the nitrogen to which they are attached to form a ring;

R$^{13}$ is a member selected from the group consisting of substituted or unsubstituted alkyl, substituted or unsubstituted cycloalkyl, substituted or unsubstituted aryl, substituted or unsubstituted heteroaryl, substituted or unsubstituted aralkyl, substituted or unsubstituted heterocyclyl, substituted or unsubstituted heteroalkyl, substituted or unsubstituted heteroaryl-heteroalkyl, and substituted or unsubstituted aryl-heteroalkyl;

b is an integer from 1 to 2; and
d is an integer from 0 to 2.

15. The compound according to claim 1, having a structure which is a member selected from the group consisting of:

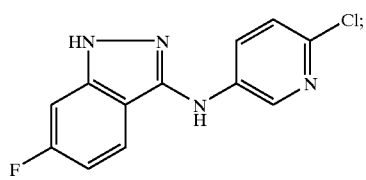

-continued

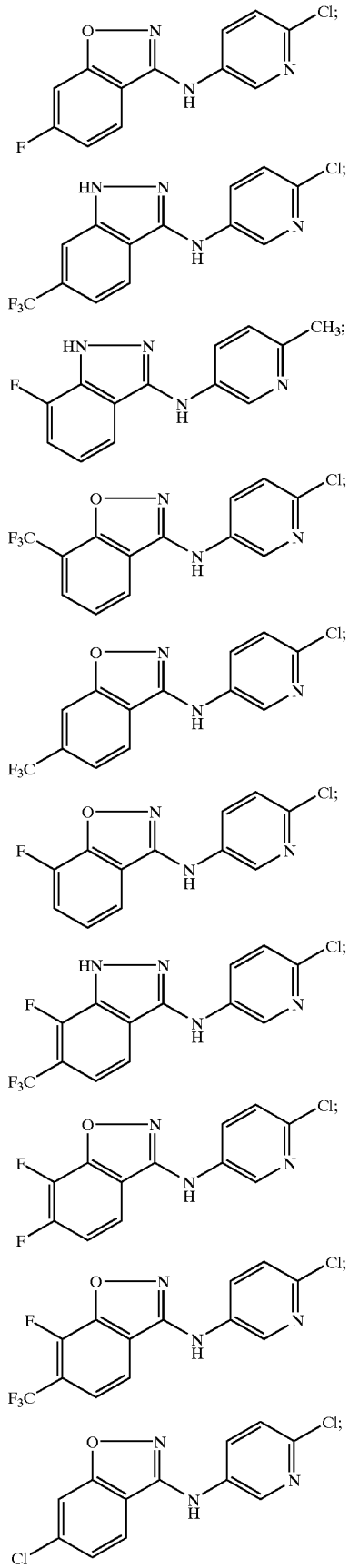

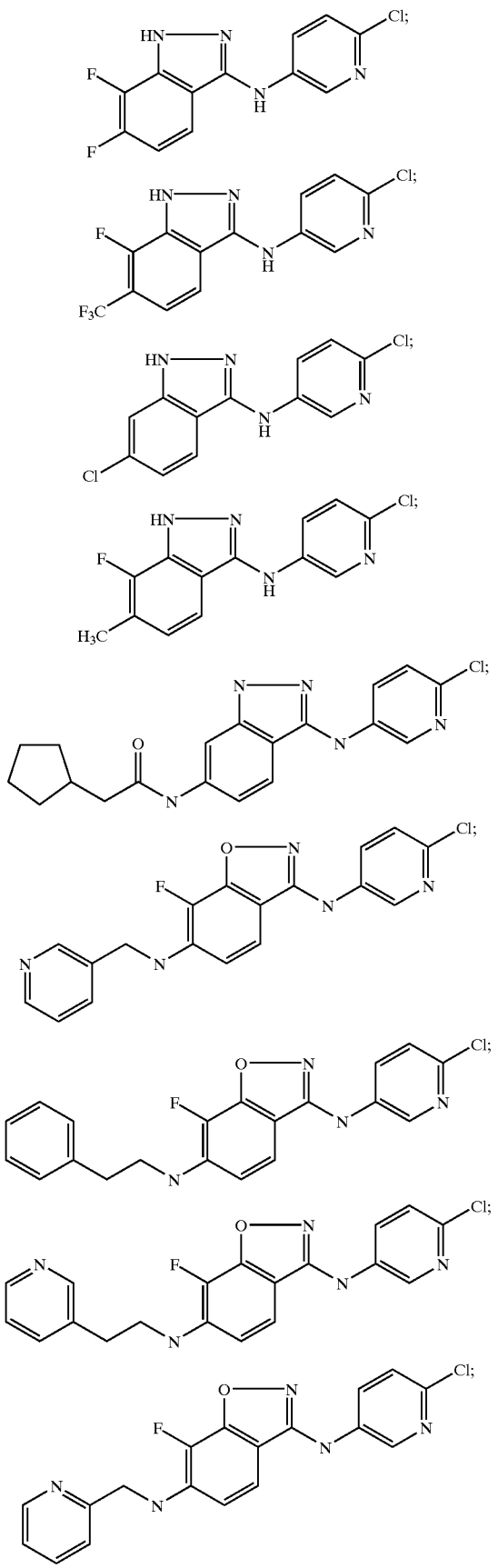

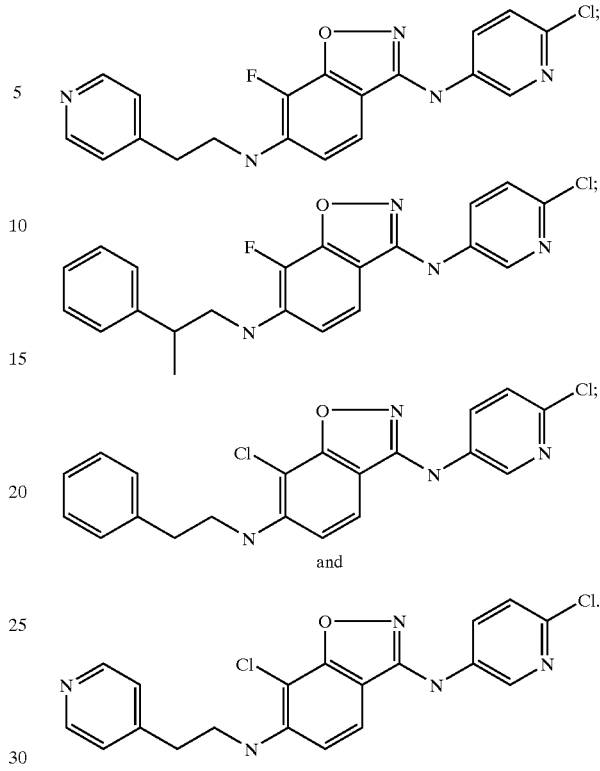

and

16. A composition for increasing ion flow in a voltage-dependent potassium channel, said composition comprising a pharmaceutically acceptable excipient and a compound having the structure:

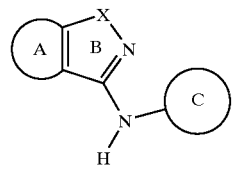

wherein,
ring A is fused to ring B and is a member selected from substituted or unsubstituted aryl groups, and five- and six-membered, substituted or unsubstituted heteroaryl rings;
ring C is a heteroaromatic ring, which is a member selected from the group consisting of:

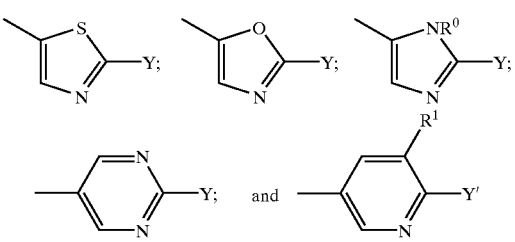

wherein,
Y is a member selected from the group consisting of halogen, $R^2$, and $OR^2$;
$R^0$, $R^1$ and $R^2$ are members independently selected from the group consisting of H and substituted or unsubstituted alkyl;

Y' is a member selected from the group consisting of halogen, R$^{2'}$, and OR$^2$;

R$^{2'}$ is substituted or unsubstituted alkyl;

X is a member selected from the group consisting of —NR$^3$, —O—, and —S—; and

R$^3$ is a member selected from the group consisting of H, SO$_2$R$^4$, substituted or unsubstituted alkyl and substituted or unsubstituted cycloalkyl, wherein R$^4$ is a member selected from the group consisting of substituted or unsubstituted alkyl and substituted or unsubstituted cycloalkyl.

17. The composition according to claim 16, wherein at least one member of said ring A bears a substituent bound thereto that is a member selected from the group consisting of halogen, —CN, —NO$_2$, —NR$^5$R$^6$, NR$^5$C(O)$_q$R$^7$, —NR$^5$S(O)$_s$R$^7$, —OR$^5$, —C(O)$_2$R$^5$, —C(O)R$^7$, —S(O)$_s$R$^7$, —R$^5$, —C(O)$_q$NR$^5$R$^6$ and —SO$_2$NR$^5$R$^6$;

R$^5$ and R$^6$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;

R$^7$ is a member selected from the group consisting of substituted or unsubstituted alkyl, substituted or unsubstituted cycloalkyl, substituted or unsubstituted aryl, substituted or unsubstituted heteroaryl, substituted or unsubstituted aralkyl, substituted or unsubstituted heterocyclyl, substituted or unsubstituted heteroalkyl, substituted or unsubstituted heteroaryl-heteroalkyl, and substituted or unsubstituted aryl-heteroalkyl;

s is a member selected from the group consisting of the integers from 0 to 2; and q is a member selected from the group consisting of the integers from 1 to 2.

18. The composition according to claim 17, wherein R$^5$ and a member selected from the group consisting of R$^6$ and R$^7$ of said substituent are joined to form a ring system.

19. The composition according to claim 17, wherein said ring A bears at least two of said substituents, wherein said substituents are bound to adjacent members of said ring A and at least two of said substituents are joined together to form at least one ring system.

20. The composition according to claim 19, wherein said at least one ring system is a member selected from the group consisting of substituted or unsubstituted (C$_1$–C$_7$) carbocyclyl, and substituted or unsubstituted heterocyclyl having a ring size of from 5 to 7 members.

21. The composition according to claim 16, wherein ring C is a pyridyl ring.

22. The composition according to claim 16, wherein Y is a member selected from the group consisting of H, halogen, CH$_3$, OCH$_3$, CF$_3$ and OCF$_3$.

23. The composition according to claim 22, wherein Y is a member selected from the group consisting of F, Cl, and CH$_3$.

24. The composition according to claim 16, wherein X is a member selected from the group consisting of —O—, —S—, and —N(H)—.

25. The composition according to claim 24, wherein Y is a member selected from the group consisting of H, halogen, CH$_3$, OCH$_3$, CF$_3$ and OCF$_3$.

26. The composition according to claim 25, wherein Y is a member selected from the group consisting of F, Cl, and CH$_3$.

27. The composition according to claim 16, wherein ring A is a five- or six-membered heteroaromatic ring containing at least one substituted or unsubstituted carbon atom other than the carbon atoms at the fusion of rings A and B, and up to 2 heteroatoms, which are members independently selected from the group consisting of -O—, —S—, =N—, and —N(R$^{14}$)—; and R$^{14}$ is a member selected from the group consisting of H and substituted or unsubstituted alkyl.

28. The composition according to claim 16, wherein said ring A is a member selected from the group consisting of substituted benzo and substituted pyridyl groups.

29. The composition according to claim 28, wherein ring A is:

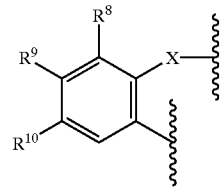

wherein,

R$^8$, R$^9$ and R$^{10}$ are members independently selected from the group consisting of H, halogen, substituted or unsubstituted alkyl, C(O)$_b$R$^{11}$, C(O)NR$^{11}$R$^{12}$, SO$_2$NR$^{11}$R$^{12}$, NR$^{12}$R$^{13}$, S(O)$_d$R$^{13}$, OR$^{13}$, NHR$^{13}$, CN, and fluoroalkyl wherein, R$^{11}$ and R$^{12}$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl, and R$^{11}$ and R$^{12}$ together with the nitrogen to which they are attached are optionally joined to form a ring;

R$^{13}$ is a member selected from the group consisting of substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;

b is an integer from 1 to 2; and d is an integer from 0 to 2.

30. The composition according to claim 16, wherein said compound has a structure that is a member selected from the group consisting of:

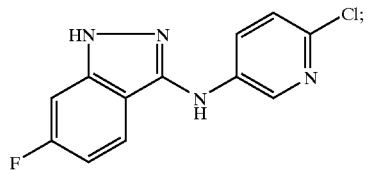

-continued
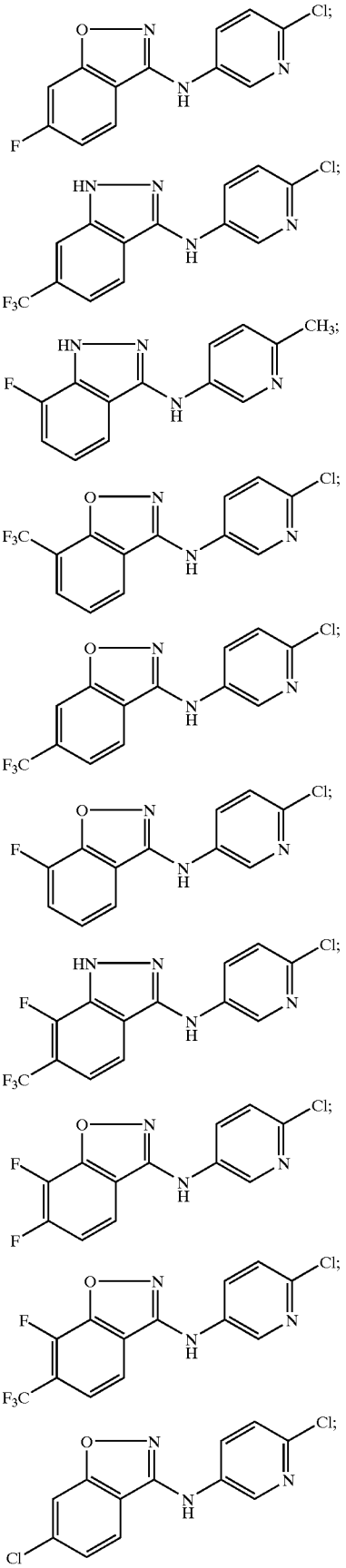
-continued
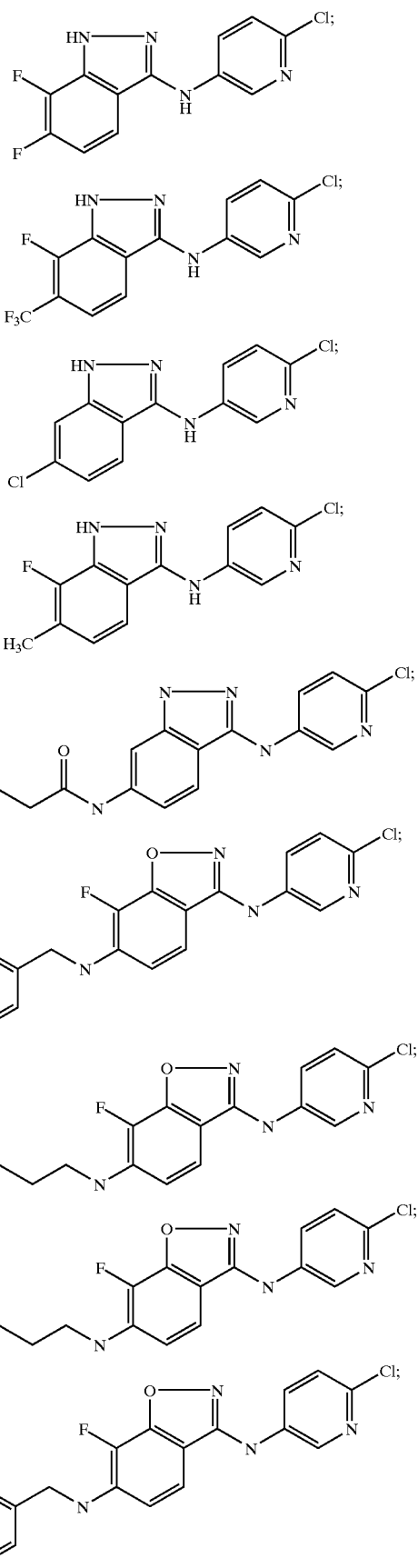

31. A method of increasing ion flow through voltage-dependent potassium channels in a cell, said method comprising contacting said cell with a potassium channel opening amount of a compound having the structure:

wherein,
ring A is fused to ring B and is a member selected from substituted or unsubstituted aryl groups, and five- and six-membered, substituted or unsubstituted heteroaryl rings;
ring C is a heteroaromatic ring, which is a member selected from the group consisting of:

wherein,
Z is a member selected from the group consisting of $NR^o$, S and O;
D is a member selected from the group consisting of N and $CR^1$;
Y is a member selected from the group consisting of halogen, $R^2$, and $OR^2$;
$R^o$, $R^1$ and $R^2$ are members independently selected from the group consisting of H and substituted or unsubstituted alkyl;

X is a member selected from the group consisting of $-NR^3$, $-O-$, and $-S-$; and
$R^3$ is a member selected from the group consisting of H, $SO_2R^4$, substituted or unsubstituted alkyl and substituted or unsubstituted cycloalkyl, wherein $R^4$ is a member selected from the group consisting of substituted or unsubstituted alkyl and substituted or unsubstituted cycloalkyl.

32. The method according to claim 31, wherein at least one member of said ring A bears a substituent bound thereto that is a member selected from the group consisting of halogen, $-CN$, $-NO_2$, $-NR^5R^6$, $-NR^5C(O)_qR^7$, $-NR^5S(O)_qR^7$, $-OR^5$, $-C(O)_2R^5$, $-C(O)R^7$, $-S(O)_sR^7$, $-R^5$, $-C(O)_qNR^5R^6$ and $-SO_2NR^5R^6$;
$R^5$ and $R^6$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;
$R^7$ is a member selected from the group consisting of substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;
s is a member selected from the group consisting of the integers from 0 to 2; and
q is a member selected from the group consisting of the integers from 1 to 2.

33. The method according to claim 32, wherein $R^5$ and a member selected from the group consisting of $R^6$ and $R^7$ of said substituent are joined to form a ring system.

34. The method according to claim 32, wherein said ring A bears at least two of said substituents, wherein said substituents are bound to adjacent members of said ring A and at least two of said substituents are joined together to form at least one ring system.

35. The method according to claim 34, wherein said at least one ring system is a member selected from the group consisting of substituted or unsubstituted ($C_1$-$C_7$) carbocyclyl, and substituted or unsubstituted heterocyclyl having a ring size of from 5 to 7 members.

36. The method according to claim 31, wherein ring C is a pyridyl ring.

37. The method according to claim 31, wherein Y is a member selected from the group consisting of H, halogen, $CH_3$, $OCH_3$, $CF_3$ and $OCF_3$.

38. The method according to claim 37, wherein Y is a member selected from the group consisting of F, Cl, and $CH_3$.

39. The method according to claim 31, wherein X is a member selected from the group consisting of $-O-$, $-S-$, and $-N(H)-$.

40. The method according to claim 39, wherein Y is a member selected from the group consisting of H, halogen, $CH_3$, $OCH_3$, $CF_3$ and $OCF_3$.

41. The method according to claim 40, wherein Y is a member selected from the group consisting of F, Cl, and $CH_3$.

42. The method according to claim 31, wherein ring A is a five- or six-membered heteroaromatic ring containing at least one substituted or unsubstituted carbon atom other than the carbon atoms at the fusion of rings A and B, and up to 2 heteroatoms, which are members independently selected from the group consisting of —O—, —S—, =N—, and —N(R$^{14}$)—; and R$^{14}$ is a member selected from the group consisting of H and substituted or unsubstituted alkyl.

43. The method according to claim 42, wherein said ring A is a member selected from the group consisting of substituted benzo and substituted pyridyl groups.

44. The method according to claim 43, wherein ring A is:

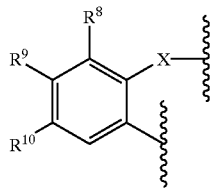

wherein,

R$^8$, R$^9$ and R$^{10}$ are members independently selected from the group consisting of H, halogen, substituted or unsubstituted alkyl, C(O)$_b$R$^{11}$, C(O)NR$^{11}$R$^{12}$, NR$^{12}$R$^{13}$, SO$_2$NR$^{11}$R$^{12}$, S(O)$_d$R$^{13}$, OR$^{13}$, NHR$^{13}$, CN, and fluoroalkyl wherein, R$^{11}$ and R$^{12}$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl, and R$^{11}$ and R$^{12}$ together with the nitrogen to which they are attached are optionally joined to form a ring;

R$^{13}$ is a member selected from the group consisting of substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;

b is an integer from 1 to 2; and d is an integer from 0 to 2.

45. The method according to claim 31, wherein said compound has a structure which is a member selected from the group consisting of:

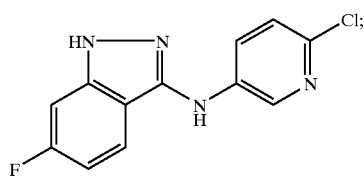

-continued

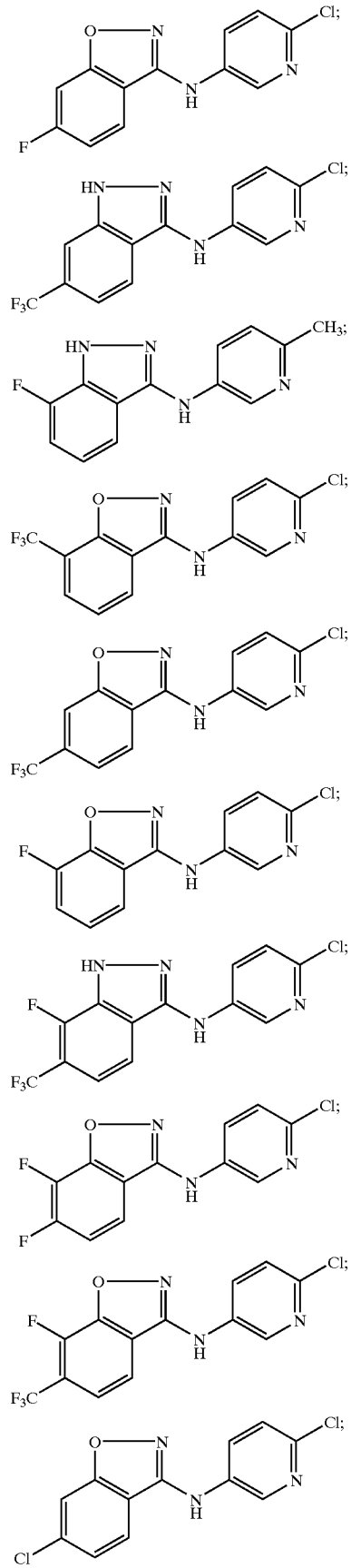

-continued

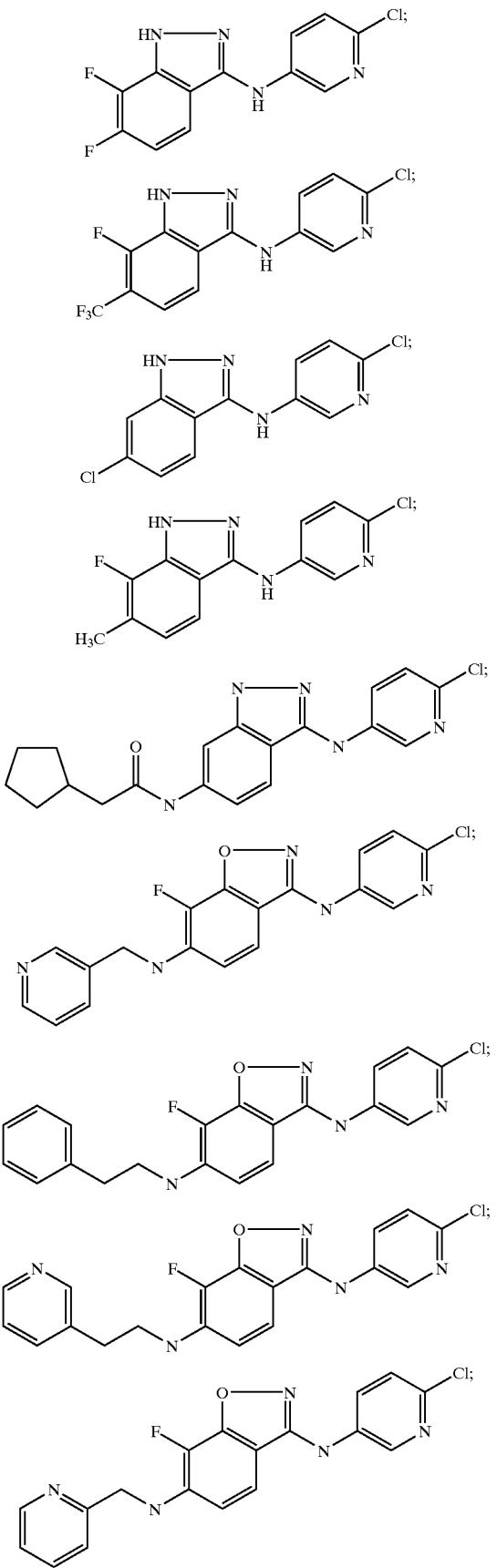

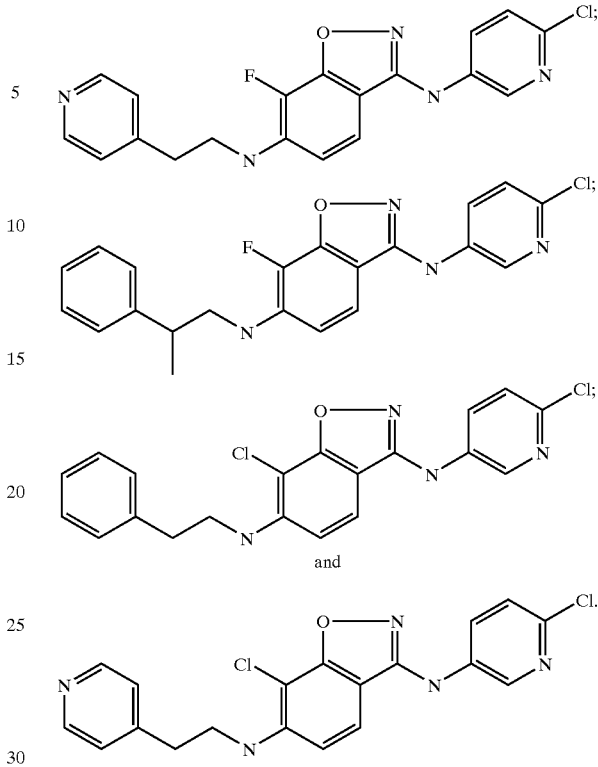

46. A method of treating a central or peripheral nervous system disorder or condition through modulation of a voltage-dependent potassium channel, said method comprising administering to a subject in need of such treatment, an effective amount of a compound having the structure:

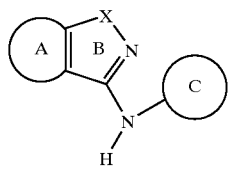

wherein,
  ring A is fused to ring B and is a member selected from substituted or unsubstituted aryl groups, and five- and six-membered, substituted or unsubstituted heteroaryl rings;
  ring C is a heteroaromatic ring, which is a member selected from the group consisting of:

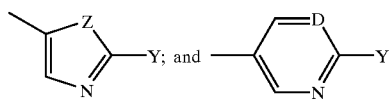

wherein,
  Z is a member selected from the group consisting of $NR^o$, S and O;
  D is a member selected from the group consisting of N and $CR^1$;
  Y is a member selected from the group consisting of halogen, $R^2$, and $OR^2$;
  $R^o$, $R^1$ and $R^2$ are members independently selected from the group consisting of H and substituted or unsubstituted alkyl;

X is a member selected from the group consisting of —NR$^3$, —O—, and —S—; and

R$^3$ is a member selected from the group consisting of H, SO$_2$R$^4$, substituted or unsubstituted alkyl and substituted or unsubstituted cycloalkyl, wherein R$^4$ is a member selected from the group consisting of substituted or unsubstituted alkyl and substituted or unsubstituted cycloalkyl.

47. The method according to claim 46, wherein at least one member of said ring A bears a substituent bound thereto that is a member selected from the group consisting of halogen, —CN, —NO$_2$, —NR$^5$R$^6$, —NR$^5$C(O)$_q$R$^7$, —NR$^5$S(O)$_s$R$^7$, —OR$^5$, —C(O)$_2$R$^5$, —C(O)R$^7$, —S(O)$_s$R$^7$, —R$^5$, —C(O)$_q$NR$^5$R$^6$ and —SO$_2$NR$^5$R$^6$;

R$^5$ and R$^6$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;

R$^7$ is a member selected from the group consisting of substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;

s is a member selected from the group consisting of the integers from 0 to 2; and q is a member selected from the group consisting of the integers from 1 to 2.

48. The method according to claim 47, wherein R$^5$ and a member selected from the group consisting of R$^6$ and R$^7$ of said substituent are joined to form a ring system.

49. The method according to claim 47, wherein said ring A bears at least two of said substituents, wherein said substituents are bound to adjacent members of said ring A and at least two of said substituents are joined together to form at least one ring system.

50. The method according to claim 49, wherein said at least one ring system is a member selected from the group consisting of substituted or unsubstituted (C$_1$–C$_7$) carbocyclyl, and substituted or unsubstituted heterocyclyl having a ring size of from 5 to 7 members.

51. The method according to claim 46, wherein ring C is a pyridyl ring.

52. The method according to claim 46, wherein Y is a member selected from the group consisting of H, halogen, CH$_3$, OCH$_3$, and OCF$_3$.

53. The method according to claim 52, wherein Y is a member selected from the group consisting of F, Cl, and CH$_3$.

54. The method according to claim 46, wherein X is a member selected from the group consisting of —O—, —S—, and —N(H)—.

55. The method according to claim 54, wherein Y is a member selected from the group consisting of H, halogen, CH$_3$, OCH$_3$, CF$_3$ and OCF$_3$.

56. The method according to claim 55, wherein Y is a member selected from the group consisting of F, Cl, and CH$_3$.

57. The method according to claim 46, wherein ring A is a five- or six-membered heteroaromatic ring containing at least one substituted or unsubstituted carbon atom other than the carbon atoms at the fusion of rings A and B, and up to 2 heteroatoms, which are members independently selected from the group consisting of —O—, —S—, =N—, and —N(R$^{14}$)—; and R$^{14}$ is a member selected from the group consisting of H and substituted or unsubstituted alkyl.

58. The method according to claim 57, wherein said ring A is a member selected from the group consisting of substituted benzo and substituted pyridyl groups.

59. The method according to claim 58, wherein ring A is:

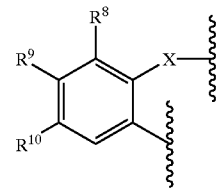

wherein,

R$^8$, R$^9$ and R$^{10}$ are members independently selected from the group consisting of H, halogen, substituted or unsubstituted alkyl, C(O)$_b$R$^{11}$, C(O)NR$^{11}$R$^{12}$, NR$^{12}$R$^{13}$, SO$_2$NR$^{11}$R$^{12}$, S(O)$_d$R$^{13}$, OR$^{13}$, NHR$^{13}$, CN, and fluoroalkyl wherein, R$^{11}$ and R$^{12}$ are members independently selected from the group consisting of H, substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl and R$^{11}$ and R$^{12}$ together with the nitrogen to which they are attached are optionally joined to form a ring;

R$^{13}$ is a member selected from the group consisting of substituted or unsubstituted alkyl, substituted or unsubstituted cycloalkyl, substituted or unsubstituted aryl, substituted or unsubstituted aralkyl, substituted or unsubstituted heteroaryl, substituted or unsubstituted heterocyclyl, substituted or unsubstituted heteroalkyl, substituted or unsubstituted heteroaryl-heteroalkyl, and substituted or unsubstituted aryl-heteroalkyl;

b is an integer from 1 to 2; and d is an integer from 0 to 2.

60. The method according to claim 46, wherein said compound has a structure which is a member selected from the group consisting of:

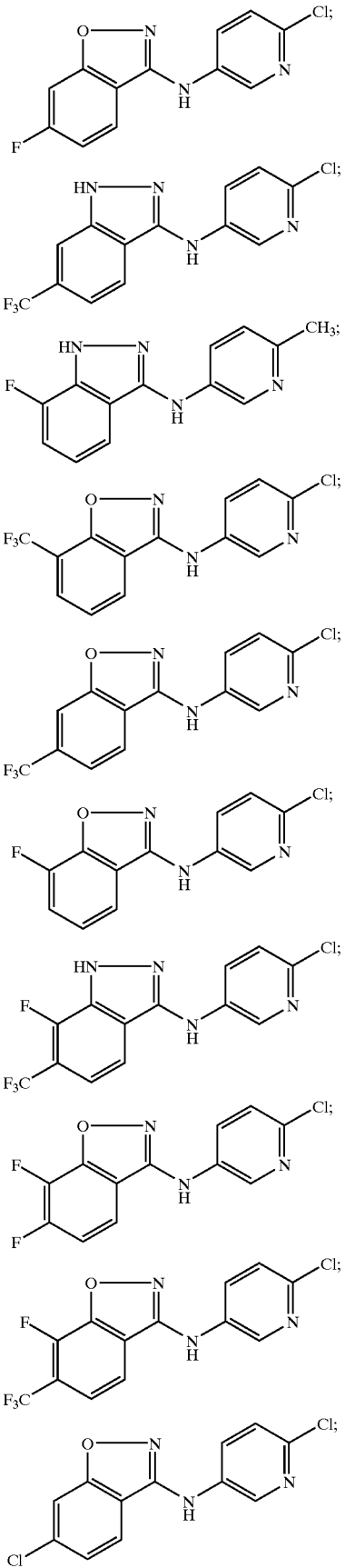
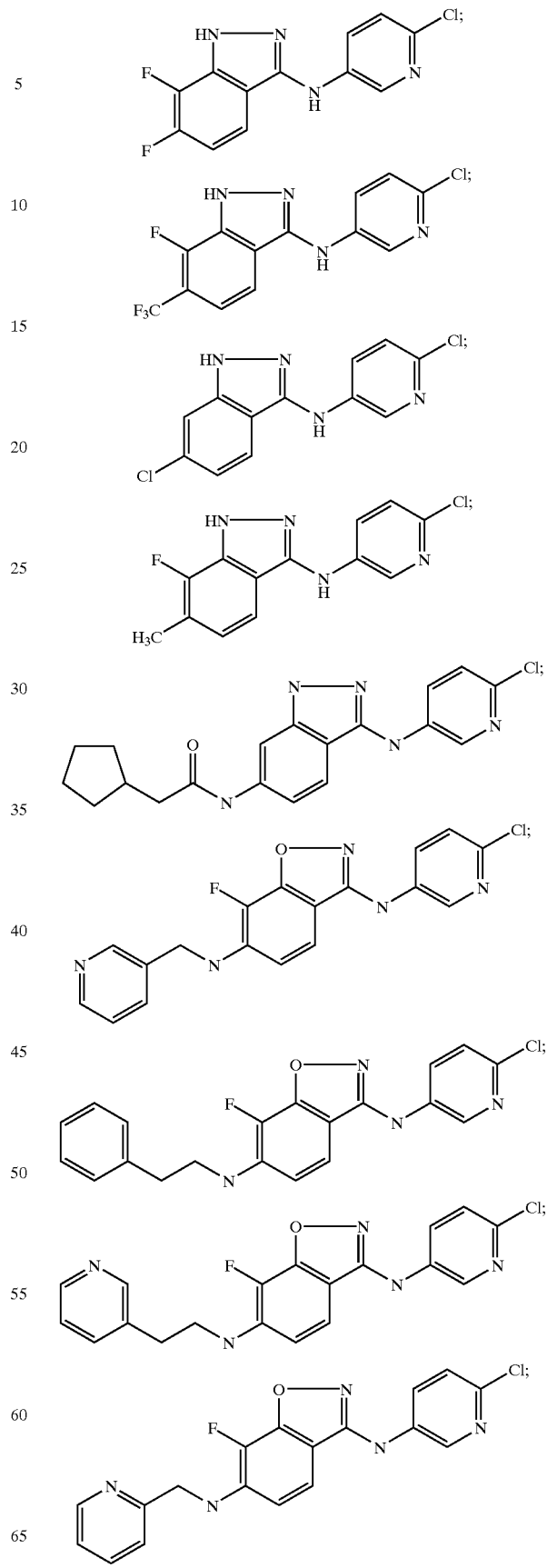

61. The method according to claim 46, wherein said disorder or condition is selected from the group consisting of migraine, ataxia, Parkinson's disease bipolar disorders, trigeminal neuralgia, spasticity, mood disorders, brain tumors, psychotic disorders, myokumia, seizures, epilepsy, hearing loss, vision loss, Alzheimer's disease, age-related memory loss, learning deficiencies, anxiety, motor neuron diseases, and stroke.

62. The method in accordance with claim 61, wherein said condition or disorder is epilepsy or sizures.

63. The method in accordance with claim 61, wherein said condition or disorder is hearing loss.

64. The method in accordance with claim 61, wherein said condition or disorder is pain or anxiety.

65. A method of treating a member selected from the group consisting of pain, anxiety and bipolar disorder through modulation of a voltage-dependent potassium channel, said method comprising administering to a subject in need of such treatment, an effective amount of a compound having the structure:

wherein,
ring A is fused to ring B and is a member selected from substituted or unsubstituted aryl groups, and five- and six-membered, substituted or unsubstituted heteroaryl rings;
ring C is a heteroaromatic ring, which is a member selected from the group consisting of:

wherein,
Z is a member selected from the group consisting of $NR^o$, S and O;
D is a member selected from the group consisting of N and $CR^1$;
Y is a member selected from the group consisting of halogen, $R^2$, and $OR^2$;
$R^o$, $R^1$ and $R^2$ are members independently selected from the group consisting of H and substituted or unsubstituted alkyl;
X is a member selected from the group consisting of —$NR^3$, —O—, and —S—; and
$R^3$ is a member selected from the group consisting of H, $SO_2R^4$, substituted or unsubstituted alkyl and substituted or unsubstituted cycloalkyl, wherein $R^4$ is a member selected from the group consisting of substituted or unsubstituted alkyl and substituted or unsubstituted cycloalkyl.

66. A compound having the structure:

wherein,
ring A is fused to ring B and is a member selected from the group consisting of substituted benzo and substituted pyridyl groups;
ring C is a heteroaromatic ring, which is a member selected from the group consisting of:

wherein,
Z is a member selected from the group consisting of $NR^o$, S and O;
D is a member selected from the group consisting of N and $CR^1$;
Y is a member selected from the group consisting of halogen, $R^2$, and $OR^2$;
$R^o$, $R^1$ and $R^2$ are members independently selected from the group consisting of H and substituted or unsubstituted alkyl;
X is a member selected from the group consisting of —$NR^3$, —O—, and —S—; and
$R^3$ is a member selected from the group consisting of H, $SO_2R^4$, substituted or unsubstituted alkyl and substituted or unsubstituted cycloalkyl, wherein $R^4$ is a member selected from the group consisting of substituted or unsubstituted alkyl and substituted or unsubstituted cycloalkyl.

67. A composition for increasing ion flow in a voltage-dependent potassium channel, said composition comprising a pharmaceutically acceptable excipient and a compound having the structure:

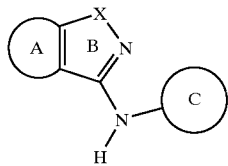

wherein,
ring A is fused to ring B and is a member selected from the group consisting of substituted benzo and substituted pyridyl groups;
ring C is a heteroaromatic ring, which is a member selected from the group consisting of:

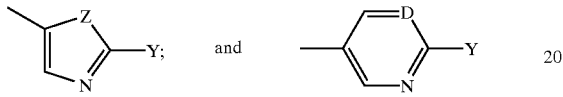

wherein,
Z is a member selected from the group consisting of $NR^o$, S and O;
D is a member selected from the group consisting of N and $CR^1$;
Y is a member selected from the group consisting of halogen, $R^2$, and $OR^2$;
$R^o$, $R^1$ and $R^2$ are members independently selected from the group consisting of H and substituted or unsubstituted alkyl;
X is a member selected from the group consisting of —$NR^3$, —O—, and —S—; and
$R^3$ is a member selected from the group consisting of H, $SO_2R^4$, substituted or unsubstituted alkyl and substituted or unsubstituted cycloalkyl, wherein $R^4$ is a member selected from the group consisting of substituted or unsubstituted alkyl and substituted or unsubstituted cycloalkyl.

* * * * *